US008329194B2

(12) United States Patent
Brownlie et al.

(10) Patent No.: US 8,329,194 B2
(45) Date of Patent: Dec. 11, 2012

(54) VACCINE COMPOSITION FOR VACCINATING DOGS AGAINST CANINE INFECTIOUS RESPIRATORY DISEASE (CIRD)

(75) Inventors: John Brownlie, Herts (GB); Victoria Jane Chalker, Herts (GB); Kerstin Erles, Herts (GB)

(73) Assignee: The Royal Veterinary College, Hatfield, Hertfordshire (GB)

( * ) Notice: Subject to any disclaimer, the term of this patent is extended or adjusted under 35 U.S.C. 154(b) by 0 days.

(21) Appl. No.: 10/563,199

(22) PCT Filed: Jul. 1, 2004

(86) PCT No.: PCT/GB2004/002865
§ 371 (c)(1),
(2), (4) Date: Sep. 1, 2006

(87) PCT Pub. No.: WO2005/002618
PCT Pub. Date: Jan. 13, 2005

(65) Prior Publication Data
US 2007/0098739 A1    May 3, 2007

(30) Foreign Application Priority Data
Jul. 1, 2003    (GB) .................. 0315323.6

(51) Int. Cl.
*A61K 39/09*    (2006.01)
(52) U.S. Cl. .................................................. 424/244.1
(58) Field of Classification Search ............... 424/244.1
See application file for complete search history.

(56) References Cited

U.S. PATENT DOCUMENTS

| | | | | |
|---|---|---|---|---|
| 4,567,042 A * | 1/1986 | Acree et al. ............... | 424/202.1 |
| 4,824,785 A * | 4/1989 | Acree et al. ............... | 435/237 |
| 4,944,942 A * | 7/1990 | Brown et al. ............... | 424/244.1 |
| 5,583,014 A * | 12/1996 | Brown et al. ............... | 435/71.2 |
| 5,661,006 A * | 8/1997 | Brown et al. ............... | 435/69.3 |
| 5,665,363 A * | 9/1997 | Hansen et al. ............... | 424/211.1 |
| 5,672,350 A | 9/1997 | Parker et al. | |
| 5,750,112 A | 5/1998 | Gill | |
| 5,753,235 A * | 5/1998 | Haanes et al. ............... | 424/229.1 |
| 5,916,570 A | 6/1999 | Kapil | |
| 6,057,436 A | 5/2000 | Miller et al. | |
| 6,080,725 A * | 6/2000 | Marciani ..................... | 514/26 |
| 6,248,329 B1 * | 6/2001 | Chandrashekar et al. . | 424/191.1 |
| 6,280,974 B1 | 8/2001 | Miller et al. | |
| 6,372,224 B1 | 4/2002 | Miller et al. | |
| 6,682,745 B1 * | 1/2004 | Jacobs et al. ............... | 424/244.1 |
| 2002/0150593 A1 * | 10/2002 | Hymas et al. ............... | 424/201.1 |
| 2003/0021801 A1 | 1/2003 | Stephens et al. | |
| 2003/0039667 A1 * | 2/2003 | Jira et al. ..................... | 424/274.1 |

FOREIGN PATENT DOCUMENTS

| EP | 0 109 942 A2 | 5/1984 |
|---|---|---|
| EP | 0 180 564 A2 | 5/1986 |
| EP | 0 231 039 A1 | 1/1987 |
| EP | 0 415 794 A1 | 3/1991 |
| EP | 0415794 A1 * | 9/1991 |
| EP | 04157941 * | 9/1991 |
| EP | 0 510 773 A1 | 10/1992 |
| EP | 1 023 903 A1 | 8/2000 |
| GB | 2189141 A | 10/1987 |
| GB | EP 0415794 A1 * | 9/1991 |
| GB | EP 04157941 * | 9/1991 |
| WO | WO 86/02355 A1 | 4/1986 |
| WO | WO 87/00531 A1 | 1/1987 |
| WO | WO 93/23423 A1 | 11/1993 |
| WO | WO 98/16643 A1 | 4/1998 |
| WO | WO 99/25838 A1 | 5/1999 |
| WO | WO 2004/011651 A1 | 2/2004 |
| WO | WO 2004/032957 A1 | 4/2004 |

OTHER PUBLICATIONS

Colman et al. (Research in Immunology 145: 33-36, 1994.*
Erles et al Arch Virol 2005 vol. 150 pp. 1493-1504.*
Plotkin and Mortimer Vaccines (Ellis Chapter 29 of Vaccines), Plotkin, et al. (eds) WB Saunders, Philadelphia, 1998.*
Hechard et al 2003 Journal of Medical Microbiology vol. 52 pp. 35-40.*
Bowie et al (Science, 1990, 247:1306-1310).*
Senyk et al (Medical Microbiology Immunology vol. 168 pp. 91-101 1980).*
Angus, J.C. et al. 1997 "Microbiological study of transtracheal aspirates from dogs with suspected lower respiratory tract disease: 264 cases (1989-1995)." *J. Am. Vet. Med. Assoc.* 210:55-58.
Anzai, T. et al. 2000 "Comparison of the phenotypes of *Streptococcus zooepidemicus* isolated from tonsils of healthy horses and specimens obtained from foals and donkeys with pneumonia." *Am. J. Vet. Res.* 61:162-166.
Appel, M. et al. 1987 "Canine infectious tracheobronchitis short review: kennel cough". In: Appel M. (Ed.), *Virus Infections of Carnivores.* Elsevier. Oxford. pp. 201-211.
Appel, M.J.G. et al. 1970 "SV-5-like parainfluenza virus in dogs." *J. Am. Vet. Med. Assoc.* 156:1778-81.
Arizmendi, F. et al. 1992 "Isolation of *Chlamydia psittaci* from pleural effusion in a dog." *J Vet Diagn Invest.* 4:460-3. Balaguer, P. et al. 1991 "Quantification of DNA sequences obtained by polymerase chain reaction using a bioluminescence adsorbent." *Anal. Biochem.* 195:105-110.
Balter, S. et al. 2000 "Epidemic nephritis in Nova Serrana, Brázil." *The Lancet* 355:1776-1780.
Barile, M.F. 1985 "Immunization against mycoplasma infections" In: S. Razin and M.F. Barile (Ed.) *The Mycoplasmas*, vol. 4. Mycoplasma pathogenicity. Academic Press, Inc, Orlando, Florida, pp. 451-492.
Barile, M.F. et al. 1985 "Current status on the controls of mycoplasma diseases of man, animals, plants and insects." *Bull. Inst. Pasteur.* 83: 339-373.
Barron A.L. (Ed.) 1988 *Microbiology of Chlamydia* Boca Raton, CRC Press., pp. 168-169.
Becker, D.M. et al. 1990 "High-efficiency transformation of yeast by electroporation." *Methods Enzymol.* 194:182-187.
Beggs, J.D. 1978 "Transformation of yeast by a replicating hybrid plasmid." *Nature* 275:104-109.

(Continued)

*Primary Examiner* — Gary Nickol
*Assistant Examiner* — Nina Archie
(74) *Attorney, Agent, or Firm* — Knobbe Martens Olson & Bear LLP

(57) ABSTRACT

A vaccine composition for vaccinating dogs comprising any one or more of (a) an agent capable of raising an immune response against *Streptococcus equi* sub species *zooepidemicus* in a dog, (b) an agent capable of raising an immune response against *Mycoplasma cynos* in a dog, and (c) an agent capable of raising an immune response against a *Chlamydophila* in a dog.

13 Claims, 9 Drawing Sheets

OTHER PUBLICATIONS

Bemis, D.A. et al. 1977 "Naturally occurring respiratory disease in a kennel caused by *Bordetella bronchiseptica*." *Cornell Vet*. 67:282-293.

Bemis, D.A. et al. 1977 "Pathogenesis of canine bordetellosis." *J. Infect. Dis* 135:753-762.

Better, M. et al. 1988 "*Escherichia coli* secretion of an active chimeric antibody fragment." *Science* 240:1041-1043.

Bhugra, B. et al. 1995 "Identification and chracterization of genome rearrangements", Chapter B9, in: Razin & Tully (Eds.) Genome Characterisation and Genetics, Section B in *Molecular and Diagnostic Procedures in Mycoplasmology*. vol. 1. Academic Press Inc., pp. 195-199.

Biberstein, E.L. et al. 1980 "Serogroups and biostypes among beta-hemolytic *streptococci* of canine origin." *J. Clin. Microbiol*. 11:558-561.

Biberstein, E.L. et al. 1999 "*Streptococci*". In: Hirsh, D.C., Zee, Y.C., (Eds.) *Veterinary Microbiology* Blackwell Science, Oxford, pp. 120-126.

Binn, L.N. et al. 1967 "Viruses recovered from laboratory dogs with respiratory disease." *Proc. Soc. Exp. Biol. Med*. 126:140-145.

Binn, L.N. et al. 1979 "Studies of respiratory disease in random-source laboratory dogs: viral infections in unconditioned dogs." *Lab. Anim. Sci*. 29: 48-52.

Bird, R.E et al. 1988 "Single-chain antigen-binding proteins." *Science* 242:423-426.

Cavanagh, D. et al. "Coronviridae" in "*Virus Taxonomy*, 6th Report of the International Committee on Taxonomy of Viruses", Eds. Murphy et al., springer-Verlag Wein, New York, pp. 407-411.

Chalker, V.J. et al. 2003 "Respiratory disease in kennelled dogs: serological responses to *Bordetella bronchiseptica* lipopolysaccharide do not correlate with bacterial isolation or clinical respiratory symptoms." *Clin. Diagn. Lab Immunol*. 10(3):352-6.

Chalker, V.J. et al. 2003 "The association of *Streptococcus equi* subsp. *zooepidemicus* with canine infectious respiratory disease." *Veterinary Microbiol*. 95:149-156.

Chanter, N. 1997 "Streptococci and enterococci as animal pathogens." *J. Appl. Microbiol. Symp*. Suppl. 83:100S-109S.

Chilvers, M.A. 2001 "The effects of coronavirus on human nasal ciliated respiratory epithelium." *Eur. Respir. J*. 18:965-70.

Cohen, S.N. et al. 1972 "Nonchromosomal Antibiotic Resistance in Bacteria: Genetic Transformation of *Escherichia coli* by R-Factor DNA." *PNAS USA* 69:2110-2114.

Compton, J. 1991 "Nucleic acid sequence-based amplification." *Nature* 350:91-92.

Corcoran, B. 1998 "Cytological collection techniques." In: Luis Fuentes, V. Swift, S., (Eds.), *Manual of small animal cardiorespiratory medicine and surgery* British Small Anim. Vet. Assoc. Cheltenham. pp. 75-78.

Coyne, M.J. et al. 1995 "Considerations in using a canine coronavirus vaccine" (published as a Pfizer Technical Bulletin on the Internet at http://www.pfizer.com/ah/vet/tref/trbull/ ccv.html), pp. 1-6.

Database Phin online 2002 "Nobivac Forcat in Switzerland" *Veterinaria News* online 2002 (German language document).

Dicesare, B. et al. 1993 "A high-sensitivity electrochemiluminescence-based detection system for automated PCR product quantitation." *BioTechniques* 15:152-157.

Ditchfield, J. et al. 1962 "Association of a canine adenovirus (Toronto A 26/61) with an outbreak of laryngotracheitis ("kennel cough")." *Can. Vet. Jour*. 3(8): 238-247.

Durgut, R. et al. 2003 "Kennel cough syndrome of dogs observed in Ankara province." *Indian Vet. J*. 80: 743-745.

Dybvig, K. et al. 1995 "Artificial transformation of mollicutes via polyethylene glycol- and electroporation-mediated methods", Chapter B7 in: Razin & Tully (Eds.) Genome Characterisation and Genetics, Section B in *Molecular and Diagnostic Procedures in Mycoplasmology*. vol. 1. Academic Press Inc., pp. 179-184.

Dybvig, K. et al. 1995 "Characterization of virus genomes and extrachromosomal elements", Chapter B5 in Razin & Tully (Eds.) "Genome Characterisation and Genetics", Section B in *Molecular and Diagnostic Procedures in Mycoplasmology*. vol. 1. Academic Press Inc., pp. 159-166.

Ellis, J.A. et al. 2001 "Effect of vaccination on experimental infection with *Bordetella bronchiseptica* in dogs." *J. Am. Vet. Med. Assoc*. 218(3):367-75.

Erles, K. et al. 2003 "Detection of a group 2 coronavirus in dogs with canine infectious respiratory disease." *Virology* 310:216-223.

Everett, K.D. et al. 1999 "Emended description of the order *Chlamydiales*, proposal for *Parachlamydiacease* fam. Nov. and *Simkaniaceae* Fam. Nov., each containing one monotypic genus, revised taxonomy of the family *Chlamydiaceae*, including a new genus and five new species, and standards for the identification of organisms" *Int. J. Syst. Bacteriol*. 49:415-440.

Farrow, J.A. et al. 1984 "Taxonomic studies on Streptococci of serological groups C, G and L and possibly related taxa." *Syst. Appl. Microbiol*. 5:483-493.

Felsenstein, J. 1989 "PHYLIP-Phylogeny Inference Package (Version 3.2c) " *Cladistics* 5:164-166.

Fraser, G et al. 1969 "A case history of psittacosis in the dog." *Vet. Rec*. 85(3):54-58.

Fukushi, H et al. 1992 "Proposal of *Chlamydia pecorum* sp. nov. for *Chlamydia* strains derived from ruminants" *Int. J. Syst. Bacteriol*. 42:306-308.

Fukushi, H. et al. 1985 "Seroepidemiological surveillance of *Chlamydia psittaci* in cats and dogs in Japan." *Vet Rec*. 117: 503-4.

Garnett, N.L. 1982 "Hemorrhagic streptococcal pneumonia in newly procured research dogs." *J. Am. Vet. Med. Assoc*. 181:1371-1374.

GCG Manual, version 10.3: Section of the Program Manual for the GCG Package, Version 10.3, relating to the GAP alignment (Genetics Computer Group (1982-2002), 575 Science Drive, Madison, Wisconsin, USA 53711), 14 pages (http://helix.nih.gov/docs/gcg/gap. html).

Genbank Accession No. AF058942, 1991 "Bovine coronavirus strain LY-138 32 kDa putative non-structural protein, hemagglutinin esterase (HE), spike glycoprotein (s), 4.9 kDa putative non-structural protein, 12.7 kDa non-structural protein, structural protein E (E), structural protein M (M), structural protein N (N), and I protein (I) genes, complete cds.", 6 pages.

Genbank Accession No. AAM 77000, 2002 "Spike glycoprotein [Porcine hemagglutinating encephalomyelitis virus].", 2 pages.

Genbank Accession No. AF124985 1999 "Bovine coronavirus RNA-directed RNA polymerase (pol) gene, partial cds.", 2 pages.

Genbank Accession No. AF124986 1999 "Canine coronavirus RNA-directed RNA polymerase (pol) gene, partial cds.", 2 pages.

Genbank Accession No. AF124989 1999 "Human coronavirus (strain OC43) RNA-directed RNA polymerase (pol) gene, partial cds.", 2 pages.

Genbank Accession No. AF220295, 1999 "Bovine coronavirus strain Quebec, complete genome.", 14 pages.

Genbank Accession No. AF481863, 2002 "Porcine hemagglutinating encephalomyelitis virus HE glycoprotein, spike glycoprotein (S), 4.9 kDa nonstructural protein (ns4.9), matrix glycoprotein (M), phosphorylated nucleocapsid protein N, and N2 (N2) genes, complete cds.", 5 pages.

Genbank Accession No. L07747, 1994 "Human enteric coronavirus 4408 hemagglutinin-esterase (HE) gene sequence.", 2 pages.

Genbank Accession No. L14643, 1993 "Human coronavirus OC43 spike protein, complete cds." 3 pages.

Genbank Accession No. M76373, 1992 "Huuman coronavirus OC43 hemagglutinin-esterase (HE) gene, complete cds.", 2 pages.

Genbank Accession No. M84486, 1993 "Bovine coronavirus strain LY138 hemagglutinin/esterase glycoprotein (HE) gene.", 2 pages.

Genbank Accession No. Z32768 1994 "Human coronavirus OC43 gene for surface protein", 3 pages.

Grand Laboratories, Inc. (2000) Technical Information on Scour Bos™ 4, 2 pages (http://www.grandlab.com/bioproducts).

Grayston, J.T. et al. 1989 "*Chlamydia pneumoniae* sp. nov. for *Chlamydia* sp. strain TWAR" *Int. J. Syst. Bacteriol*. 39: 88-90.

Gresham, A.C.J. et al. 1996 "Domiciliary outbreak of psittacosis in dogs: potential for zoonotic infection." *Vet. Rec*. 138(25):622-3.

Hasoksuz, M. et al. 1999 "Antigenic variation among bovine enteric coronaviruses (BECV) and bovine respiratory coronaviruses (BRCV) detected using monoclonal antibodies." *Arch. Virol*. 144(12): 2441-7.

Hechard, C. et al. 2002 "Protection evaluation against *Chlamydia abortus* challenge by DNA vaccination with a dnaK-encoding plasmid in pregnant and non-pregnant mice." *Vet. Res.* 33: 313-326.

Huston, J.S. et al. 1988 "Protein engineering of antibody binding sites: recovery of specific activity in an anti-digoxin single chain Fv analogue produced in *Escherichia coli*." *PNAS USA* 85:5879-5883.

Iacobelli, S. et al. 1988 "Measurement of a breast cancer associated antigen detected by monoclonal antibody SP-2 in sera of cancer patients." *Breast Cancer Res. Treat.* 11:19-30.

Ignjatovic, J. et al. 2000 "Avian infectious bronchitis virus." *Rev. Sci. Tech. Off. Int. Epiz.* 19:493-508.

Jacobs, K.A. et al. 1988 "The thermal stability of oligonucleotde duplexes is sequence independent in tetraalkylammonium salt solutions: application to identifying recombinant DNA clones." *Nucl. Acids Res.* 16:4637-4650.

Jalkanen, M. et al. 1985 "Heparan sulfate proteoglycans from mouse mammary epitherlial cells: localization on the cell surface with a monoclonal antibody" *J. Cell. Biol.* 101: 976-984.

Jalkanen, M. et al. 1987 "Cell surface proteoglycan of mouse mammary epithelial cells is shed by cleavage of its matrix-binding ectodomain from its membrane-associated domain" *J. Cell. Biol.* 105: 3087-3096.

Jang, S.S., et al. 1984 "Mycoplasma as a cause of canine urinary tract infection." *J. Am. Vet. Med. Assoc.* 185(1):45-7.

Karpas, A. et al. 1968 "Canine tracheobronchitis: Isolation and characterization of the agent with experimental reproduction of the disease (32618)." *Proc. Soc. Exp. Biol. Med.* 127:45-52.

Karpas, A. et al. 1968 "Experimental production of canine tracheobronchitis (kennel cough) with canine herpesvirus isolated from naturally infected dogs." *Am. J. Vet. Res.* 29(6):1251-1257.

Keil, D.J, et al. 1998 "Role of *Bordetella bronchiseptica* in infectious tracheobronchitis in dogs." *J. Am. Vet. Med. Assoc.* 15:200-207.

Kettleborough, C.A. et al. 1991 "Humanization of a mouse monoclonal antibody by CDR grafting; The importance of framework residues in loop conformation." *Protein Eng.* 14(7): 773-783.

Kirkpatrick, B.C. et al. 1995 "Isolation of Mycoplasma-like organism DNA from plant and insect hosts", Chapter B2, in Razin & Tully (Eds.) *Genome Characterisation and Genetics*, Section B in *Molecular and Diagnostic Procedures in Mycoplasmology*. vol. 1. Academic Press Inc., pp. 105-117.

Lai, M.M.C. et al. 1997 "The molecular biology of coronaviruses." in *Advances in Virus Research* Eds. Maramorosch et al., Academic Press, 48:4-22.

Lambrechts, N. et al. 1999 "*Chlamydia*-induced septic polyarthritis in a dog." *Tydskr. S. Afr. Vet. Assoc.* 70(1):40-42.

Lu, G-S et al. 1981 "Improved synthesis of 4-alkoxybenzyl alcohol resin." *J. Org. Chem.* 46:3433-3436.

Luchansky, J.B. et al. 1988 "Application of electroporation for transfer of plasmid DNA to *Lactobacillus, Lactococcus, Leuconostoc, Listeria, Pediococcus, Bacillus, Staphylococcus, Enterococcus* and *Propionibacterium*." *Mol. Microbiol.* 2:637-646.

Makela, M.J. et al. 1998 "Viruses and bacteria in the etiology of the common cold." *J. Clin. Microbiol.* 36:539-42.

McCandlish, I.A.P. et al. 1978 "A study of dogs with kennel cough." *Vet. Rec.* 102:298-301.

McKiernan, B.C. et al. 1982 "Bacterial Isolates from the lower trachea of clinically healthy dogs." *J. Am. Anim. Hospl. Assoc.* 20:139-142.

Morrison, S.L. et al. 1984 "Chimeric human antibody molecules: mouse antigen-binding domains with human constant region domains." *PNAS USA* 81:6851-6855.

National Office of Animal Health Ltd. (NOAH)(2001) "Compendium of Data Sheets for Veterinary Products 2002-2003". pp. 216-217 (Duramune); 228-231 (Kavak); 322 (Lactovac); 355-63 (Nobivac); 448-449 (Eurican); 602-4 (Vanguard); 678 (Intrac); 700-702 (Quantum); 703-705 (Rotavec); and 759-61 (Canigen).

Neimark, H. et al. 1995 "Mollicute chromosome size determination and characterization of chromosomes from uncultured mollicutes.", Chapter B3 in Razin & Tully (Eds.) Genome Characterisation and Genetics, Section B in *Molecular and Diagnostic Procedures in Mycoplasmology*. vol. 1. Academic Press Inc., pp. 119-131.

Neuberger, M.S. et al. 1998 "Antibody engineering." $8^{th}$ *International Biotechnology Symposium* Part 2, 792-799.

Obukhov, I.L. et al. 2001 "Development of vaccine against chlamydiosis in cats, dogs and fur-bearing animals." *Sel'skokhozyaistvennaya Biologiya*, 2:68-79, Biosis Database Accession No PREV200100271011 (XP-002301528), Abstract only.

Page, R.D.M. 1996 "Treeview: An application to display phylogenetic trees on personal computers." *Computer Appl. Biosci.* 12: 357-358.

Page. L.A. 1968 "Proposal for the recognition of two species in the genus *Chlamydia* Jones, Rake, and Stearns." *Int. J. Syst. Bacteriol.* 18(1): 51-66.

Pearson, W.R. et al. 1988 "Improved tools for biological sequence comparison." *PNAS USA* 85(8):2444-2448.

Pfizer Animal Health Technical Services. 2002 Label Info for Scour Guard 3K. (http://www.americanlivestock.com/showLabelInfo.jsp-?productFamilyId=1075).

Pluckthun, A. 1991 "Antibody engineering; advances from use of *Escherichia coli* expression systems." *Bio/technology* 9:545-551.

Proft, T. et al. 1995 "Physical and genetic mapping", Chapter B4 in Razin & Tully (Eds.) "Genome Characterisation and Genetics", Section B *in Molecular and Diagnostic Procedures in Mycoplasmology*. vol. 1. Academic Press Inc., pp. 133-157.

Quinn, P.J. et al. (Eds.), 1999 *In Clinical Veterinary Microbiology* published by Mosby, pp. 129-130.

Rake, G. et al. 1957 "Family II Chlamydiacae" in Breed et al. (Eds.) *Bergey's Manual of Determinative Bacteriology*, $7^{th}$ Edition, The Williams & Wilkins Co., Baltimore, USA., pp. 957-968.

Randolph, J.F. et al. 1993 "Prevalence of mycoplasmal and ureaplasmal recovery from tracheobronchial lavages and prevalence of mycoplasmal recovery from pharyngeal swab specimens in dogs with or without pulmonary disease." *Am. J. Vet. Res.* 54(3):387-91.

Razin, A. et al. 1995 "DNA methylation analysis", Chapter B8, in Razin & Tully (Eds.) "Genome Characterisation and Genetics", Section B in *Molecular and Diagnostic Procedures in Mycoplasmology*. vol. 1. Academic Press Inc., pp. 185-194.

Razin, S. 1995 "Introductory Remarks", Chapter B1 in Razin & Tully (Eds.) "Genome Characterisation and Genetics", Section B *in Molecular and Diagnostic Procedures in Mycoplasmology*. vol. 1. Academic Press Inc., pp. 101-103.

Renaudin, J. et al. 1995 "Plasmid and viral vectors for gene cloning and expression in *Spiroplasma citri*", Chapter B6 in Razin & Tully (Eds.) "Genome Characterisation and Genetics", Section B *in Molecular and Diagnostic Procedures in Mycoplasmology*. vol. 1. Academic Press Inc., pp. 167-178.

Renbaum, P. et al. 1995 "Expression of mycoplasmal genes in *Escherichia coli*", Chapter B10 in Razin & Tully (Eds.)"Genome Characterisation and Genetics", Section B in *Molecular and Diagnostic Procedures in Mycoplasmology*. vol. 1. Academic Press Inc., pp. 201-211.

Rosendal, S. 1972 "Mycoplasmas as a possible cause of enzootic pneumonia in dogs." *Acta Vet. Scand.* 13: 137-139.

Rosendal, S. 1978 "Canine mycoplasmas: pathogenicity of mycoplasmas associated with distemper pneumonia." *J. Infect. Dis.* 138:203-210.

Rosendal, S. et al. 1977 "Experimental mycoplasmal pneumonia in dogs: electron microscopy of infected tissue." *Acta Pathol. Microbiol. Scand.* [*B*] 85(6):462-5.

Sadatsune, T. et al. 1975 "Contribution to the study of haemolytic streptococci isolated from dogs." *Arq. Inst. Biol. Sao. Paulo*. 42:257-264.

Saiki, R.K. et al. 1986 "Analysis of enzymatically amplified β-globin and HLA-DQα DNA with allele-specific oligonucleotide probes." 324:163-166.

Sako, T. et al. 2002 "Chlamydial infection in canine atherosclerotic lesions." *Atherosclerosis* 162(2):253-9.

Schering-Plough Animal Health News Archives 1999 "Schering-Plough Animal Health Secures First EU Approval for One Shot Calf Scours Vaccine" Rotavec™ Corona, 2 pages, (http: //www.spah.com/usa/news/pr/pr41.cfm).

Skerra, A. et al. 1988 "Assembly of a functional immunoglobulin Fv fragment in *Escherichia coli*." *Science* 240:1038-1041.

Southern, E.M. 1975 "Detection of specific sequences among DNA fragments separated by gel electrophoresis." *J. Mol. Biol.* 98:503-517.

Spaan, W. et al. 1988 "Coronaviruses: structure and genome expression." *J Gen Virol*. 69:2939-52.

Stephensen, C.B. et al. 1999 "Phylogenetic analysis of a highly conserved region of the polymerase gene from 11 coronaviruses and development of a consensus polymerase chain reaction assay." *Virus Res*. 60:181-189.

Storz, J. et al. 2000 "Coronavirus and *Pasteurella* infections in bovine shipping fever pneumonia and Evans' criteria for causation." *J. Clin. Microbiology*. 38(9): 3291-3298.

Swango, L.J. et al. 1970 "A comparison of the pathogenesis and antigenicity of infectious canine hepatitis virus and the A26/61 virus strain (Toronto)." *J.A.V.M.A*. 156:1687-1696.

Tennant, B.J. et al. 1993 "Studies on the epizootiology of canine coronavirus." *Vet. Rec*. 132(1):7-11.

Thompson, H. et al. 1976 "Experimental respiratory disease in dogs due to *Bordetella bronchiseptica*." *Res. Vet. Sci*. 20:16-23.

Thompson, J.D. et al. 1997 "The Clustal_X windows interface: flexible strategies for multiple sequence alignment aided by quality analysis tools." *Nucleic Acids Res*. 25(24):4876-82.

Thrusfield, M.V. et al. 1991 "A field investigation of kennel cough: incubation period and clinical signs." *J. Small Anim. Pract*. 32:215-220.

Tillotson, G.S. 1982 "An evaluation of the API-20 STREP system". API*2 0 STREP: Identification system for *Streptococcaceae* and related organisms (bioMérieux˙SA) *J. Clin. Path*. 468-472.

Timoney, J.F. 1987 "The Streptococci". In: Gyles, C.L., Thoen C.O., (Eds.) *Pathogenesis of bacterial infections in animals*. Iowa State University Press., pp. 12-13.

Timoney, J.F. et al. (Eds), 1988 "The Genus *Streptococcus*". In: *Hagan and Bruner's Microbiology and Infectious Diseases of Domestic Animals*. Comstock Publishing Associates, London., pp. 181-187.

Ural, O. et al. 2003 "*Streptococcus zooepidemicus* meningitis and bacteraemia." *Scand. J. Infect. Dis*. 35(3): 206-207.

Vaccine Data Sheets 2006 COUGHGUARD-B˙ (Pfizer Animal Health); VANGUARD˙ 5/B (Pfizer Animal Health); NASAGUARD-B™ (Pfizer Animal Health); PROGARD˙—KC (Intervet); PROGARD˙—KC PLUS (Intervet)., 10 pages.

Verhoeyen, C. et al. 1988 "Reshaping human antibodies: grafting an antiysozyme activity." *Science* 239: 1534-1536.

Walker, G.T. et al. 1992 "Strand displacement amplification—an isothermal, in vitro DNA amplification technique." *Nucl. Acid Res*. 20:1691-1696.

Walker, J.A., et al. 1998 "Molecular basis of variation in protective SzP proteins of *Streptococcus zooepidemicus*" *Am. J. Vet. Res*. 59:1129-1133.

Walker, R.L. et al. 2003 "Identification of variations in SzP proteins of *Streptococcus equi* subspecies *zooepidemicus* and the relationship between protein variants and clinical signs of infection in horses." *Am. J. Vet. Res*. 64: 976-81.

Ward, E.S. et al. 1989 "Binding activities of a repertoire of single immunoglobulin variable domains secreted from *Escherichia coli*." *Nature* 341:544-546.

Werth. D., et al. 1987 "Detection of antibodies to *Chlamydia psittaci* and *Coxiella burnetii* in dogs and cats: comparison between enzyme-linked immunosorbent assay, immunoperoxidase-technique, complement fixation test and immunodiffusion test." *J. Vet. Med*. 34(3): 165-76.

Widders, P.R. et al. 1995 "Immunisation of mares to control endometritis caused by *Streptococcus zooepidemicus*." *Res. Vet. Sci*. 58: 75-81.

Winter, G. et al. 1991 "Man-made antibodies." *Nature* 349:293-299.

Woloszyn, S. et al. 1994 "Infectious tracheobronchitis in dogs" *Medycyna Wet*. 50:428-431 (Polish language document), Biosis Data base Accession No. PREV199497512573 (XP-002304443).

Wood, J.L.N. et al. 1993 "*Streptococci* and *Pasteurella* spp. associated with disease of the equine lower respiratory tract." *Equine Vet. J*. 25:314-318.

Young, S. et al. 1972 "Pathologic features of experimentally induced chlamydial infection in dogs." *Am. J. Vet. Res*. 33(2): 377-83.

API 20 Strep (Jan. 2003) "Identification system for *Streptococacaeae* and related organisms", *bioMerieux sa*, ref 20 600, 8 pages.

Azetaka, M. et al. (1988) "Kennel cough complex: confirmation and analysis of the outbreak in Japan", *Jpn. J. Vet. Sci*, 50:851-858.

Lou, T. et al. (1963) "Natural and experimental infection of dogs with reovirus, type 1: pathogenicity of the strain for other animals", *Am. J. Hyg*. 77:293-304.

Pensaert, M. (1986) "Isolation of a porcine respiratory, non-enteric coronavirus related to transmissible gastroenteritis", *The Veterinary Quarterly* 8:257-261.

Smith, J.E. (1961) "The aerobic bacteria of the nose and tonsils of healthy dogs", *J. Comp. Path*. 71:4298-433.

Binn, L.N. et al. 1968 "Upper respiratory disease in military dogs: Bacterial, mycoplasma, and viral studies" *Am J Vet Res* 29:1809-1815.

Chalker, V.J. et al. 2004 "Mycoplasmas associated with canine infectious respiratory disease" *Microbiology* 150:3491-3497.

Chalker, V.J. and Brownlie, J. 2004 "Taxonomy of the canine Mollicutes by 16S rRNA gene and 16S/23S rRNA intergenic spacer region sequence comparison" *Int J Systematic and Evolutionary Microbiol* 54:537-542.

Pfizer Product Information Sheet for Rispoval 4, http://www.noahcompendium.co.uk/Pfizer_Limited/documents/S3762.html.

Pfizer Product Information Sheet for Vanguard 7; http://www.noahcompendium.co.uk/Pfizer_Limited/documents/S3791.html.

Wagener, J.S. et al. 1984 "Role of canine parainfluenza virus and *Bordetella bronchiseptica* in kennel cough" *Am J Vet Res* 45:1862-1866.

Rosendal, S. 1982 "Canine mycoplasmas: Their ecologic niche and role in disease" *J Am Vet Med Ass* 180:1212-1214.

Woloszyn, S. and Kostro, K. 1994 "Canine Infectious Tracheobronchitis" *Medycyna Wet* 50:428-431.

Chandler, J.C. et al. 2002 "Mycoplasmal respiratory infections in small animals: 17 cases (1988-1999)" *J Amer Animal Hospital Assoc* 38:111-119.

European Search Report for European Application No. EP 08075914, dated Dec. 22, 2009.

Quinn, P.J. et al. 1994 "The Mycoplasmas (Class: Mollicutes)" *Clinical Veterinary Microbiology* pp. 320-326.

Brady, C.A. 2003 "Bacterial Pneumonia in dogs and cats" in *Textbook of Respiratory Disease in Dogs and Cats*, King, L.G. ed. Saunders, Chapter 56, pp. 412-421.

Chalker, V.J. et al. 2004 "Development of a polymerase chain reaction for the detection of *Mycoplasma felis* in domestic cats" *Veterinary Microbiology* 100:77-82.

Jameson, P.H. et al. 1995 "Comparison of clinical signs, diagnostic findings, organisms isolated, and clinical outcome in dogs with bacterial pneumonia: 93 cases (1986-1991)" *J Am Vet Med Assoc* 206:206-209.

Ford, R.B. 2003 "Infectious Traceobronchitis" in *Textbook of Respiratory Disease in Dogs and Cats*,King, L.G. ed. Saunders, Chapter 49, pp. 364-372.

Rosendal, S. 1973 "*Mycoplasma cynos*, a new canine *Mycoplasma* species" *Int J Systematic Bacteriology* 23:49-54.

Ford, R.B. & Vaden, S.L. 1998 "Canine infectious tracheobronchitis". in: *Infectious Diseases of the Cat and Dog*. 2nd edition Ed C.E. Greene. Philadelphia: W B Saunders & Co., pp. 33-38.

Vieson, M.D. et al 2012 "A review of the pathology and treatment of canine respiratory infections" *Veterinary Medicine: Research and Reports* 3:25-39.

Quinn, P.J. et al. 1994 in *Clinical Veterinary Microbiology*, Wolf Publishing, an Imprint of Mosby-Year Book Europe Limited, Spain pp. 109, 117, 320-326, 486-497 and 579-581.

* cited by examiner

FIGURE 5

```
AGTGGTCTCC CCAGATTCAG ACTAGGTTTC ACGTGCCTAG CCCTACTCAG
GTATCGAATA GAGTCTCTTG TTTTTTCGTC TACGGGACTA TCACCCTGTA
TCGTTCTACT TTCCAGAAGT ATTCGACTAA AACTTAAGAT CCCATGTTAT
CGACCCTACA ACCCCACATT AAAAATGTGG TTTGGTCTTC TCCCCTTTCG
CTCGCCGCTA CACAGGGA (SEQ ID NO: 1)
```

FIGURE 8

DHBC2
GACAGTGGTC TCCCCAGATT CAVACTAGGT TTCACGTGTC TAGCCCTACT
CAGGTATCGA ATAGAGTCTC TTGTTTTTWC GTCTACGGGA CTATCACCCT
GTATCGTTCT ACTTTCCAGA AGTATTCGAC TAAAACTTAA GATCCCATGT
TATCGACCCT ACAACCCCAC ATTAAAAATG TGGTTTGGTC TTCTCCCCTT
TCGCTCGCCG CTACACAGGG A (SEQ ID NO: 2)

DHBC4
TGAGAGTGGT CTCCCCAGAT TCAGACTAGG TTTCACGTGT CTAGCCCTAC
TCAGGTATCG AATAGAGTCT CTTGTTTTTT CGTCTACGGG ACTAACACCC
TGTATCGTTC TACTTTCCAG AAGTATTCGA CTAAAACTTA AGATCCCATG
TTATCGACCC TACAACCCCA CATTAAAAAT GTGGTTTGGT CTTCTCCCCT
TTTCGCTCGK CCGYTATCAX CAGGG (SEQ ID NO: 3)

DHBC5
GADAGTGGTC TCCCCAGATT CADACTAGGT TTCACGTGTC TAGCCCTACT
CAGGTATCGA ATAGAGTCTC TTGTTTTTTC GTCTACGGGA CTATCACCCT
GTATCGTTCT ACTTTYCAGA AGTATTCGAC TAAWWCTTAA GATCCCATGT
TATCGACCCT ACAACCCCAC ATTWWWWATG TGGTTTGGTC TTCTCCCCTT
TYGCTCGCCG CTACACAGGG A (SEQ ID NO: 4)

DHBC6
TGAGAGTGGT CTCCCCAGAT TCAGACTAGG TKtCACGTGT CTAGCCCTAC
TCAGGTATCG AATAGAGTCT CTTGTTTTKT CGTCTACGGG ACTATCACCC
TGTATCGTTC TACTTTCCCA GAAGTATTCG ACTAAAAHCT TAAGATcCCC
ATGTTATCGA CCCTACAAcC CCCACATDAA AAATGTGGTT TGGTCTTCTC
CCCTTTCGCT CGCCGCT (SEQ ID NO: 5)

DHBC7
GABAGTGGTC TCCCCAGATT CAGACTAGGT TTCACGTGTC TAGCCCTACT
CAGGTATCGA ATAGAGTCTC TTGTTTTTTC GTCTACGGGA CTATCACCCT
GTATCGTTCT ACTTTCCAGA AGTATTCGAC TAAAACTTAA GATCCCATGT
TATCGACCCT ACAACCCCAC ATTAAAAATG TGGTTTGGTC TTCTCCCCTT
TCGCTCGCCG CTACTCAGGG A (SEQ ID NO: 6)

DHBC8
TGAGAGTGGT CTCCCCAGAT TCAGTCAAAA TATCACGTGT TCCGACCTAC
TCAGGATACT ATTAGTATTA TTGAGAATBT TAATTACAGG AGTATCACCT
TCTATGCTCT AGTTCCAAC TAATTCATCT ATTCTCTTTA ATTACACATT
ATAGTCCTAC AAcCCCCMAA TGCAAGCATT GGGTTTGTCC TAATCCCAGT
TCGCTCGCCG CTACACAGGG (SEQ ID NO: 7)

DHBC9
TGAGAGTGGT CTCCCCAGAT TCAGACTAGG TTTCACGTGT CTAGCCCTAC
TCAGGTATCG AATAGAGTCT CTTGTTTTTT TGTCTACGGG ACTATCACCC
TGTATCGTTC TACTTTCCAG AAGTATTCGA CTAAAACTTA AGATCCCATG
TTATCGACCC TACAACCCCA CATXAAAAAT GTGGTTTGGT CTTCTCCCCT
TTCGCTCGCC GCTACACAGG (SEQ ID NO: 8)

VACCINE COMPOSITION FOR VACCINATING DOGS AGAINST CANINE INFECTIOUS RESPIRATORY DISEASE (CIRD)

RELATED APPLICATIONS

This application is a U.S. National Phase of International Patent Application No.: PCT/GB2004/002865, filed Jul. 1, 2004, designating the U.S. and published in English on Jan. 13, 2005 as WO 2005/002618, which claims the benefit of British Patent Application No.: 0315323.6, filed Jul. 1, 2003.

FIELD OF THE INVENTION

The present invention relates to a vaccine composition, and in particular to a vaccine composition for use against canine infectious respiratory disease.

BACKGROUND OF THE INVENTION

Canine infectious respiratory disease (CIRD) is a highly contagious disease common in dogs housed in crowded conditions such as re-homing centres and boarding or training kennels. Many dogs suffer only from a mild cough and recover after a short time, however in some cases a severe bronchopneumonia can develop (Appel and Binn, 1987). CIRD is rarely fatal but it delays re-homing of dogs at rescue centres and it causes disruption of schedules in training kennels as well as considerable treatment costs.

The pathogenesis of CIRD is considered to be multifactorial, involving several viruses and bacteria. The infectious agents considered to be the major causative pathogens of CIRD are canine parainfluenzavirus (CPIV) (Binn et al, 1967), canine adenovirus type 2 (CAV-2) (Ditchfield et al, 1962), and canine herpesvirus (CHV) (Karpas et al, 1968a and 1986b), canine respiratory coronavirus (CRCV) (WO 2004/011651 (The Royal Veterinary College) and Erles et al, 2003) and the bacterium *Bordetella bronchiseptica* (*B. bronchiseptica*) (Bemis et al, 1977a, Keil et al, 1998).

These viruses and bacterium have frequently been isolated during outbreaks and have been shown to cause respiratory symptoms or lung lesions in experimental infections (Appel and Percy 1970, Swango et al, 1970, Karpas et al, 1986b).

Also, human reovirus and mycoplasma species have been isolated from dogs with symptoms of CIRD (Lou and Wenner 1963, Randolph et al, 1993) Additional factors like stress may also be important.

*B. bronchiseptica* was reported as being a primary etiological agent in the respiratory disease "kennel cough" (Bemis et al, 1977b and Thompson et al, 1976). It predisposes dogs to the influence of other respiratory agents and frequently exists concurrently with them. Kennel cough can be reproduced by challenge with virulent *B. bronchiseptica*. Further, environmental factors such as cold, drafts, and high humidity, often typical conditions in dog kennels, increase susceptibility to the disease (Ellis et al, 2001). Antibiotics are generally recognised as poor agents to treat the primary disease (Ellis et al, 2001). In contrast, immunoprophylaxis for *B. bronchiseptica* provides a relatively effective means to aid in the control of disease.

The outstanding sign of *B. bronchiseptica* infection is a harsh, dry cough, which is aggravated by activity or excitement. The coughing occurs in paroxysms, followed by retching or gagging in attempts to clear small amounts of mucus from the throat. Body temperature may be elevated as secondary bacterial invasion takes place. Because kennel cough is highly contagious, the disease can readily be transmitted to susceptible dogs and produce a severe cough. The most severe signs are noted beginning two to five days following infection, but can continue for extended periods. Stress, particularly of adverse environmental conditions, may cause relapse during later stages of the disease.

Kennel cough is typically a condition of the upper airways and is characterised by nasal discharge and coughing. Whereas kennel cough mainly involves upper respiratory tract changes, the pathology of CIRD indicates that it is involved in lung damage and, in some cases, bronchopneumonia. Kennel cough is a milder syndrome than CIRD and does not have the wide range of pathology noted in CIRD. CIRD is also distinguished by an increased severity and mortality.

CIRD is a syndrome in dogs which present with respiratory signs ranging from mild to fatal disease. It is characterised by involvement of upper and lower airway infection with progression from inflammatory to exudative, oedematous and sometimes haemorrhagic pathology which can be widespread within the lung tissues. CIRD can also occur in the absence of *B. bronchiseptica*, and indeed some dogs contract CIRD whilst having no detectable *B. bronchiseptica*, which indicates that kennel cough and CIRD are distinct infections.

We have also confirmed the association of *B. bronchiseptica* with respiratory disease while concluding that other agents are involved in respiratory disease (Chalker et al, 2003).

We have now shown that *Streptococcus equi* sub species *zooepidemicus* (see Example 1), *Mycoplasma cynos* (see Example 2), and a *Chlamydophila* (see Example 3) are associated with CIRD. As all the dogs in our study populations were vaccinated against CPIV and CAV-2, we have no new data to support the involvement of these viruses in CIRD. However we have also found an increased prevalence of canine herpesvirus in dogs with more severe respiratory symptoms (see Example 4).

*Streptococcus equi* sub species *zooepidemicus* (*S. zooepidemicus*) is an opportunist pathogen which is frequently isolated from a variety of animal hosts, not only from horses. It is often found as a commensal of the upper respiratory tract mucosa of mammals (Timoney et al, 1988; Quinn et al, 1999) and has been associated with several disease syndromes including lower airway disease, foal pneumonia and cervicitis in horses (Chanter, 1997; Biberstein and Hirsh, 1999), pneumonia in llamas (Biberstein and Hirsh, 1999), septicaemia and arthritis in pigs (Timoney, 1987), mastitis in cows and goats (Timoney et al, 1988), septicaemia in poultry, pericarditis and pneumonia in lambs (Timoney, 1987), lymphadenitis in guinea pigs (Quinn et al, 1999), glomerulonephritis in humans (Balter et al, 2000) and meningitis in humans (Ural et al, 2003). In dogs *S. zooepidemicus* has been associated with wound infections and septicaemia (Quinn et al, 1999) and acute necrotising haemorrhagic pneumonia (Garnett et al, 1982).

Although dogs in the latter stages of of hemorrhagic streptococcal pneumoniae (HSP) share some histological features with dogs with CIRD, this is not the case in its early stages (see Chalker et al, 2003) and septic thrombi are present in HSP (Garnett et al, 1982). HSP has a rapid onset that was fatal in most cases without clinical signs, whereas with CIRD we see a slow onset with a huge range of clinical signs from nasal discharge, coughing, sneezing, retching, inappetance, pneumonia and bronchopneumonia.

*Mycoplasma cynos* (*M. cynos*) has been associated with canine urinary tract infection (Jang et al, 1984). It has also been identified in the lungs of a dog with distemper (Rosendal, 1978), and endobronchial inoculation of *M. cynos* was found to induce pneumonia in dogs (Rosendal & Vinther, 1977).

The canine distemper described by Rosendal (1978) is a complex disease following infection with canine distemper virus, various mycoplasma species and the bacterium *Pseudomonas*. This is a powerful combination of microbial challenges and, not surprisingly, results in pneumonia. The proportion of pathology due to the *Mycoplasma* spp. was not clear. Subsequent challenge with *M. cynos* was characterised by no signs of illness in the dogs although some local small inflammatory lesions were noted in 4 out of the 5 dogs inoculated. The significance of *M. cynos* in this syndrome was, as Rosendal stated, "difficult to assess".

The *Chlamydophila* species associated with CIRD is very closely related to *Chlamydophila abortus* (*C. abortus*) by comparison of a 218 nucleotide sequence in the 23S rRNA gene. The nucleotide sequence of this region in this *Chlamydophila* species (SEQ ID NO: 1) is over 99% identical to that of *C. abortus*, 98.6% identical to *Chlamydophila psittaci* and 96.3% identical to *Chlamydophila felis*.

The *Chlamydophila* species was identified in the trachea and lungs of dogs with CIRD. By contrast, infection with *C. abortus* is typically associated with reproductive disorders, often leading to unwanted abortion, especially in sheep. *C. abortus* has not previously been described as having a role in respiratory infection in dogs.

There are very few publications regarding *Chlamydiae* species infecting dogs, and therefore very little is known of the biodiversity of canine *Chlamydiae* species. Recently, *Chlamydia pneumoniae* (*C. pneumoniae*) has been associated with athrosclerosis in dogs (Sako et al, 2002). An unidentified *Chlamydophila* spp has also been identified in a dog with septic polyarthritis (Lambrechts et al, 1999).

*C. psittaci* has previously been isolated from faeces, brain, liver, spleen, kidney and lung tissue of household dogs (Arizmendi et al, 1992; Fraser et al, 1985 and Gresham et al, 1996). Studies have demonstrated that 20% of the pet canine population in Germany and 10% in Japan have been exposed to and raised antibodies to *Chlamydiaceae* (Werth et al, 1987 and Fukushi et al, 1985). The prevalence of *C. psittaci* seropositive dogs in the UK is unknown (Gresham et al, 1996). Dogs infected with *C. psittaci* may develop sub-clinical chronic infections, athrosclerosis, arthritis, conjunctivitis or even respiratory disease (Gresham et al, 1996 and Storz 1988). Gresham et al, (1996) isolated *C. psittaci* from a dog with symptoms of respiratory disease although these symptoms were not as severe as those in CIRD. It has been suggested that dogs may be potential reservoirs and, thereby, important in the epidemiology of human *Chlamydiae* infections (Gresham et al, 1996; Werth 1989). There is only one documented case of isolation in cell culture of *C. psittaci* from a naturally infected dog (Arizmendi et al, 1992), and one case of isolation from experimentally infected dogs (Young et al, 1972).

Vaccines are available against some of the infectious agents associated with CIRD, namely *B. bronchiseptica* as well as CPIV and CAV-2. However, despite the use of these vaccines, CIRD is still prevalent in kennels world-wide, which is possibly due to the vaccines not providing protection against all the infectious agents involved in CIRD.

SUMMARY OF THE INVENTION

A first aspect of the invention thus provides a vaccine composition for vaccinating dogs comprising any one or more of:

(a) an agent capable of raising an immune response in a dog against *S. zooepidemicus*;

(b) an agent capable of raising an immune response in a dog against *M. cynos*; and (c) an agent capable of raising an immune response in a dog against a *Chlamydophila*.

It is appreciated that the composition may contain any two of these agents, for example (a) and (b), (a) and (c), or (b) and (c). The composition may contain all three of these agents (a), (b) and (c).

By an agent capable of raising an immune response in a dog against a particular organism, we include the meaning that, when administered to a dog which is not immunocompromised or immunosuppressed, the agent induces the dog's immune system to produce antibodies which specifically bind to the organism. Thus the agent is capable of inducing a protective immune response against the particular organism.

Preferably, the antibody thus produced specifically binds the particular organism with a greater affinity than for any other molecule in the individual. Preferably, the antibody binds the particular organism with at least 2, or at least 5, or at least 10 or at least 50 times greater affinity than for any other molecule in the individual. More preferably, the antibody binds the particular organism with at least 100, or at least 1,000, or at least 10,000 times greater affinity than for any other molecule in the individual.

By an agent capable of raising an immune response in a dog against a particular organism, we also include the meaning that, when administered to a dog which is not immunocompromised or immunosuppressed, the agent induces the dog's immune system to produce antibodies which specifically bind to macromolecules such as proteins that are secreted from the organism. The antibodies would specifically bind the secreted macromolecule, such as a toxin or hemolysin, and inactivate it, therefore reducing pathogenic changes in the host and disease severity, thus allowing the host to overcome infection. Thus, by an agent capable of raising an immune response in a dog against a particular organism we include agents which are capable of raising an immune response to a part of the organism such as a secreted macromolecule.

Typically, an agent capable of raising an immune response against *S. zooepidemicus* in a dog comprises inactivated or attenuated *S. zooepidemicus*, or an immunogenic fragment of *S. zooepidemicus* or a derivative thereof, or a nucleic acid encoding said fragment or said derivative (in which case said fragment or said derivative comprises a polypeptide).

*Streptococcus equi* sub species *zooepidemicus* has been deposited at NCTC (Deposit No. 4676. S34), the ATCC (Deposit No. 43079) and the National Collection of Dairy Organisms (NCDO) (Deposit No. 1358), and is described by Farrow et al (1984).

By an "inactivated" component of a vaccine we include the meaning that the particular vaccine component, such as a bacteria, mycoplasma or virus, has been treated in such a way as to eliminate its capacity to cause disease, but still retains its ability to evoke protective immunity. By an "inactivated" vaccine component we include a killed organism.

Methods for inactivating and killing organisms such as bacteria, mycoplasma and viruses for use in a vaccine are well known in the art, and have been used, for example, in the preparation of some of the components for the dog vaccines described below.

There are several methods for inactivating micro-organisms for vaccine preparations. The simplest method is heat killing (for example, heating viruses to 58° C. for 30 minutes; boiling bacteria for 5 minutes or heating to 65° C. for 1 hour)

or killing by mixing with formalin. You can also kill microorganisms with a range of other chemicals, or by treatment with UV light.

By an "attenuated" component of a vaccine we include the meaning that the particular vaccine component, such as a bacteria, mycoplasma or virus, has been selected or otherwise treated in such a way as to greatly diminish its capacity to cause disease but still retains its ability to evoke protective immunity.

Methods for attenuating organisms such as bacteria, mycoplasma and viruses for use in a vaccine are well known in the art, and have been used, for example, in the preparation of some of the components for the dog vaccines described below.

You can attenuate microorganisms by prolonged passage in a different setting—ie cell culture for viruses or *Chlamydophila*, and on solid medium or a different host for bacteria, until a decline in virulence is noted. Alternatively you can point-mutate or delete specific genes in bacteria which are involved in virulence thus limiting the pathogenic potential of the organism, or mutate the organism so that it has a specific requirement for a chemical that is not present in the animal host and therefore cannot multiply and survive once in the host. Attenuation can also be performed in bacteria with chemical treatment and UV light treatment to cause point mutations in the genome.

An immunogenic fragment of *S. zooepidemicus* may be any fragment of *S. zooepidemicus* capable of raising a protective immune response in a dog. Thus when an immunogenic fragment of *S. zooepidemicus* is administered to a dog which is not immunocompromised or immunosuppressed, it induces the dog's immune system to produce antibodies which specifically bind to *S. zooepidemicus*.

Typically, the immunogenic fragment of a particular organism is a protein component of that organism. By a "protein component" of an organism we include the meaning of an entire protein, or a portion of a protein. It is appreciated that the protein fragment may or may not be glycosylated. Thus by "protein" we also include glycoprotein. The amino acid sequence of a glycoprotein refers to the amino acid sequence of the polypeptide backbone of the glycoprotein, irrespective of the type, number, sequence and position of the sugars attached thereto.

*S. zooepidemicus* proteins include the cell surface protein precursors (Genbank Accession Nos. AAA86832 and BAD00711), Cpn60 (Genbank Accession No. AAM88472), M-like protein (Genbank Accession Nos. AAP33082, AAP33081, AAP33080, AAP33079, AAP22285, AAB92635, AAB92634, AAB92633, AAB92632, AAB92631, AAB92630, AAB92629, AAB92628, AAB92627, AAB92626, AAB92625, AAB92624, AAB92623, AAB92622, 2111310A and BAD00712), M-like protein precursor (Genbank Accession No. AAD37432), M-like protein Szp2 precursor (Genbank Accession No. AAF75674), M-like protein Szp3 precursor (Genbank Accession No. AAF75675), M-like protein Szp4 precursor (Genbank Accession No. AAF75676), the protein similar to *Streptococcus pneumoniae* ORF5 (Genbank Accession No. BAB16041), the putative metal binding/adhesin protein (Genbank Accession No. CAB56710), zoocin A immunity factor (Genbank Accession No. AAC46073) and the Szp proteins described by Walker et al (1998, 2003; including Genbank Accession Nos. AAQ08488-AAQ08510).

Preferably, the immunogenic fragment of *S. zooepidemicus*, is a structural protein of *S. zooepidemicus* or an immunogenic portion thereof. More preferably, the immunogenic fragment of *S. zooepidemicus* is a secreted toxin, or hemolysin, or an adhesion/surface protein, or an immunogenic portion thereof.

Additional surface proteins can be isolated from a bacteria such as *S. zooepidemicus* by standard methods known to a person of skill in the art. Sambrook et al (2001) "*Molecular Cloning, a Laboratory Manual*", 3$^{rd}$ edition, Sambrook et al (eds), Cold Spring Harbor Laboratory Press, Cold Spring Harbor, N.Y., USA, incorporated herein by reference, describes general bacterial cloning techniques that would be used for this purpose.

If the agent capable of raising an immune response in a dog is a component of an organism, such as a protein, it may be isolated from a culture of the organism. More preferably, proteins are made by expression of a suitable DNA construct encoding the protein using recombinant DNA technology.

Suitable techniques for cloning, manipulation, modification and expression of nucleic acids, and purification of expressed proteins, are well known in the art and are described for example in Sambrook et al (2001), incorporated herein by reference.

Alternatively, proteins may be made using protein chemistry techniques for example using partial proteolysis of isolated proteins (either exolytically or endolytically), or by de novo synthesis. Peptides may be synthesised by the Fmoc-polyamide mode of solid-phase peptide synthesis as disclosed by Lu et al (1981) *J. Org. Chem.* 46, 3433 and references therein.

By "a derivative" of an immunogenic fragment of an organism we include the meaning of a protein, or portion of a protein, which has been modified from the form in which it is naturally present in that organism, but which retains the ability to raise an immune response in a dog, such as the ability to induce the production of antibodies that specifically bind to that organism.

For example, a derivative may include a sequence variant of the protein or portion thereof which can be used to induce the production of antibodies which specifically bind to that organism. Typically, amino acid substitutions are made to improve the antigenicity of the vaccine. Preferably, the sequence variant is at least 90%, or at least 91%, or at least 92%, or at least 93%, or at least 94%, or at least 95% identical to the native sequence of that protein or portion thereof. More preferably, the sequence variant is at least 96%, or at least 97%, or at least 98%, or at least 99%, or at least 99.5% identical to the native sequence of that protein or portion thereof.

The percent sequence identity between two polypeptides may be determined using suitable computer programs, for example the GAP program of the University of Wisconsin Genetic Computing Group. The percentage identity between two nucleotide or two amino acid sequences can be determined using GCG version 10 (Genetics Computer Group, (1991), Program Manual for the GCG Package, Version 7, April 1991, 575 Science Drive, Madison, Wis., USA 53711). The GCG parameters used can be: Gap creation penalty 50, gap extension penalty 3 for DNA, and Gap creation penalty 8 and Gap extension penalty 2 for Protein. The percentage identity between two nucleotide or two amino acid sequences can also be determined using FASTA version 34 (Pearson W R. (1990) "Rapid and sensitive sequence comparison with FASTP and FASTA". *Methods Enzymol.*; 183:63-98). FASTA settings may be Gap open penalty −16 and Gap extension penalty −4.

It will be appreciated that percent identity is calculated in relation to polypeptides whose sequence has been aligned optimally.

The alignment may alternatively be carried out using the Clustal W program (Thompson et al., (1994) *Nucleic Acids Res* 22, 4673-80). The parameters used may be as follows:

Fast pairwise alignment parameters: K-tuple (word) size; 1, window size; 5, gap penalty; 3, number of top diagonals; 5. Scoring method: x percent.

Multiple alignment parameters: gap open penalty; 10, gap extension penalty; 0.05. Scoring matrix: BLOSUM.

Typically, the sequence variant has fewer than 100, or fewer than 50, or fewer than 40, or fewer than 30, or fewer than 20 amino acid residues different from the native sequence of that protein or portion thereof. More preferably, the sequence variant has 15 or 14 or 13 or 12 or 11 or 10 or 9 or 8 or 7 or 6 or 5 or 4 or 3 or 2 or only 1 amino acid residues different from the native sequence of that protein or portion thereof.

The sequence of the derivative may have been altered to enhance the immunogenicity of the agent, or it may have no effect on its immunogenicity. For example, the derivative may have had one or more amino acid sequences that are not necessary to immunogenicity removed.

By "derivative" we also include peptides in which one or more of the amino acid residues are chemically modified, before or after the peptide is synthesised, providing that the function of the peptide, namely the production of specific antibodies in vivo, remains substantially unchanged. Such modifications include forming salts with acids or bases, especially physiologically acceptable organic or inorganic acids and bases, forming an ester or amide of a terminal carboxyl group, and attaching amino acid protecting groups such as N-t-butoxycarbonyl. Such modifications may protect the peptide from in vivo metabolism. The peptides may be present as single copies or as multiples, for example tandem repeats. Such tandem or multiple repeats may be sufficiently antigenic themselves to obviate the use of a carrier. It may be advantageous for the peptide to be formed as a loop, with the N-terminal and C-terminal ends joined together, or to add one or more Cys residues to an end to increase antigenicity and/or to allow disulphide bonds to be formed. If the peptide is covalently linked to a carrier, preferably a polypeptide, then the arrangement is preferably such that the peptide of the invention forms a loop.

According to current immunological theories, a carrier function should be present in any immunogenic formulation in order to stimulate, or enhance stimulation of, the immune system. It is thought that the best carriers embody (or, together with the antigen, create) a T-cell epitope. The peptides may be associated, for example by cross-linking, with a separate carrier, such as serum albumins, myoglobins, bacterial toxoids and keyhole limpet haemocyanin. More recently developed carriers which induce T-cell help in the immune response include the hepatitis-B core antigen (also called the nucleocapsid protein), presumed T-cell epitopes, beta-galactosidase and the 163-171 peptide of interleukin-1. The latter compound may variously be regarded as a carrier or as an adjuvant or as both. Alternatively, several copies of the same or different peptides of the invention may be cross-linked to one another; in this situation there is no separate carrier as such, but a carrier function may be provided by such cross-linking. Suitable cross-linking agents include those listed as such in the Sigma and Pierce catalogues, for example glutaraldehyde, carbodiimide and succinimidyl 4-(N-maleimidomethyl)cyclohexane-1-carboxylate, the latter agent exploiting the —SH group on the C-terminal cysteine residue (if present).

If the peptide is prepared by expression of a suitable nucleotide sequence in a suitable host, then it may be advantageous to express the peptide as a fusion product with a peptide sequence which acts as a carrier. Kabigen's "Ecosec" system is an example of such an arrangement.

Typically, the polynucleotide encoding the immunogenic fraction of *S. zooepidemicus* encodes a structural protein, and more preferably a surface protein of *S. zooepidemicus*, or an immunogenic portion thereof, or a derivative thereof. The sequences of polynucleotides encoding various *S. zooepidemicus* proteins can readily be ascertained by reference to the above Genbank Accession Nos. However, the sequence of a polynucleotide encoding any immunogenic *S. zooepidemicus* protein can readily be determined by standard molecular biology techniques.

Typically, an agent capable of raising an immune response against *M. cynos* in a dog comprises inactivated or attenuated *M. cynos*, or an immunogenic fragment of *M. cynos* or a derivative thereof, or a nucleic acid encoding said fraction or said derivative.

*Mycoplasma cynos* been deposited at NCTC (Deposit No. 10142 H831) and at the ATCC (Deposit No. 27544) and is described by Rosendal (1972).

Preferably, the immunogenic fragment of *M. cynos* is a structural protein of *M. cynos* or an immunogenic portion thereof, and more preferably, a surface protein of *M. cynos* or an immunogenic portion thereof or a derivative thereof. Surface proteins can be isolated from a mycoplasma such as *M. cynos* by standard methods known to a person of skill in the art.

Methods for identifying and isolating mycoplasma proteins are generally the same as for bacteria except that some genes may require specialised vectors that recognise the unique codon usage of mycoplasmas (see all chapters in Section B, on Genome Characterisation and Genetics, in Molecular and Diagnostic Procedures in Mycoplasmology. Vol. 1 Ed S. Razin & J. Tully. Academic Press Inc. 1995.)

The most efficacious mycoplasma vaccines tend to contain a heat- or formalin-inactivated whole cell or live attenuated vaccine, and therefore contain all, or at least the majority, of its proteins. Potential mycoplasma components for use as vaccines include proteins such the primary attachment structure membrane protein, believed to be about 45 kDA (equivalent to the P1 cytadhesin from *M. pneumoniae* and homologues such as MgPa from *M. genitalium* which are all part of a three gene operon), surface exposed proteins and other attachment proteins, membrane glycolipids, membrane polysaccharide fraction, lipoglycans and all those mentioned in the reviews of animal mycoplasma vaccines (Barile 1985 and Barile et al, 1985).

In an embodiment, the agent capable of raising an immune response against a *Chlamydophila* comprises inactivated or attenuated *C. abortus*, or an immunogenic fragment of *C. abortus* or a derivative thereof, or a nucleic acid encoding said fraction or said derivative.

*Chlamydophila abortus* (ATCC deposit no. VR-656) was deposited by Everett et al as ovine chlamydial abortion strain B-577

In another embodiment, the agent capable of raising an immune response against a *Chlamydophila* comprises inactivated or attenuated *C. psittaci*, or an immunogenic fragment of *C. psittaci* or a derivative thereof, or a nucleic acid encoding said fraction or said derivative.

*Chlamydophila psittaci*, also known as *Chlamydia psittaci*, has ATCC deposit no. VR-125 (Lillie (1930) page 1968, *Int. J. Syst. Bacteriol.* 30:274 (AL)).

In a further embodiment, the agent capable of raising an immune response against a *Chlamydophila* comprises inactivated or attenuated *C. felis*, or an immunogenic fragment of *C. felis* or a derivative thereof, or a nucleic acid encoding said fraction or said derivative.

*Chlamydophila felis* (ATCC deposit no. VR-120) was deposited by Everett et al as feline pneumonitis strain No. 1.

In another embodiment, the agent capable of raising an immune response against a *Chlamydophila* comprises inactivated or attenuated *Chlamydia muridarum* (ATCC VR 123, MoPn; Everett et al, 1999, *Int. J. Syst. Bacteriol.* 49: 431); *Chlamydia pecorum* (ATCC VR 628, Bo/E58; Fukushi and Hirai 1992, *Int. J. Syst. Bacteriol.* 42: 307); *Chlamydia pneumoniae* (Type strain: TW-183; Grayston et al, 1989, *Int. J. Syst. Bacteriol.* 39: 88); *Chlamydia suis* (ATCC VR 1474, S45; Everett et al, 1999, *Int. J. Syst. Bacteriol.* 49: 431); or *Chlamydia trachomatis* (type species) (ATCC VR 571; Busacca 1935 Rake 1957 amend. Everett et al, 1999, *Int. J. Syst. Bacteriol.* 30: 274(AL), or an immunogenic fragment thereof, or a derivative thereof, or a nucleic acid encoding said fraction or said derivative.

An immunogenic fragment of *C. abortus, C. psittaci* or *C. felis*, or of *C. muridarum, C. pecorum, C. pneumoniae, C. suis* or *C. trachomatis*, can be any fragment thereof capable of raising a protective immune response in a dog. Typically the immunogenic fragment is a protein or a portion thereof. Preferably, the immunogenic fragment is a structural protein or an immunogenic portion thereof. More preferably, the immunogenic fragment is a surface protein, or an immunogenic portion thereof or a derivative thereof. As mentioned above, surface proteins can be isolated from a bacteria such as *Chlamydophila* by standard methods known to a person of skill in the art.

*C. abortus* proteins include 60 kD heat shock protein GroEL (Genbank Accession No. AAD26144), 60 kDa cysteine-rich membrane complex protein (Genbank Accession No. AAG60550), 90-kDa protein (Genbank Accession Nos. AAC44400, AAC44401), cysteine-rich outer membrane protein Omp-2 (Genbank Accession No. AAD09597), DnaK (Genbank Accession No. AAN77259), elongation factor P (Genbank Accession No. AAK72389), GrpE (Genbank Accession No. AAN77258), HrcA (Genbank Accession No. AAN77257), major outer membrane protein (Genbank Accession Nos. AAK00237, CAA36152, CAD29327), major outer membrane protein precursor (Genbank Accession Nos. AAD29103, AAD29102, AAG53881, P16567), MutS (Genbank Accession No. AAD25864), Omp1 (Genbank Accession Nos. CAA06182, CAA06620, CAA06621, CAA06622, CAA06624, CAA06625, CAA06183, CAA06184), outer membrane protein (Genbank Accession No. AAB02850), outer membrane protein 2 (Genbank Accession No. AAD20336), POMP90A precursor (Genbank Accession No. AAC15922), POMP90B precursor (Genbank Accession No. AAC15924), POMP91A (Genbank Accession No. AAC15921), POMP91B precursor (Genbank Accession No. AAC15923), putative 98 kDa outer membrane protein (Genbank Accession No. AAB18188), putative outer membrane protein (Genbank Accession No. AAB18187), small cysteine-rich outer membrane lipoprotein (Genbank Accession No. AAG60549), sulphur-rich protein (Genbank Accession No. AAG60551), and OmpA (Genbank Accession Nos. AAT36355 and AAT36356).

*C. psittaci* proteins include 60K cysteine-rich outer membrane protein precursors (Genbank Accession Nos. P23701, B39439, JC5204 and P27606); 60K cysteine-rich proteins (Genbank Accession Nos. CAA37592 and CAA37591); chaperonin homolog (Genbank Accession No. AAB22560); early upstream open reading frame (EUO) (Genbank Accession Nos. AAA23124, Q06566 and C36909); EUO protein homologue (Genbank Accession No. JC5207); ewe abortion protein (Genbank Accession No. 1601347A); genus specific protein (Genbank Accession No. AAB22559); high molecular weight cysteine-rich envelope protein (Genbank Accession No. AAB61619); histone H1-like protein (Genbank Accession Nos. AAA23132, JH0658, Q46204); hypA protein (Genbank Accession No. JL0116); hypB protein (Genbank Accession No. JL0117); hypothetical proteins (Genbank Accession Nos. JC5206, NP_052329, NP_052332, NP_052331, NP_052330, NP_052328, NP_052327, NP_052326, NP_052325, NP_052323, CAA44340, CAA44339, CAA44334, CAA44341, CAA44338, CAA44337, CAA44336, CAA44335, CAA44332, A39999, NP_052324, CAA44333, S61492, S18143, C39999, D39999, E39999, F39999, S18148, G39999, H39999 and I39999); inclusion membrane proteins (Genbank Accession Nos. 2108371A, S61491); low molecular weight cysteine-rich envelope protein (Genbank Accession No. AAB61618); lysine-rich hypothetical protein LRO (Genbank Accession No. B36909); major outer membrane protein and precursors (Genbank Accession Nos. CAA31177, 2006276A 1616229A, AAA23148, AAA23147, AAA17396, I40864, I40740, AAA23146, CAA40300, AAK00262, AAK00250, AAK00249, AAK00248, AAK00247, AAK00246, AAK00245, AAK00244, AAK00243, AAK00242, AAK00241, AAK00240, CAC84081, A60341, A40371, B60109, A60109, MMCWPM, MMCWP3, Q00087, P10332 and AAQ91209); major sigma factor (Genbank Accession No. AAA50747); MutS (Genbank Accession Nos. AAD25866 and AAD25863); the N-terminal part of a protein of unknown function (Genbank Accession No. CAA90624); ORF 2 (Genbank Accession No. 2108371B); outer membrane protein 1 (Genbank Accession Nos. CAA76286 and CAB96859); outer membrane protein 3 precursor (Genbank Accession No. JC5203); protein of unknown function (Genbank Accession No. CAA90623); putative polymorphic membrane protein (Genbank Accession Nos. AAL36963, AAL36962, AAL36961, AAL36960, AAL36959, AAL36958, AAL36957, AAL36956, and AAL36955); small cysteine-rich envelope protein envA precursor (Genbank Accession No. A39439); sulphur-rich proteins (Genbank Accession Nos. P28164, AAB61620 and JC5205); unknown protein (Genbank Accession Nos. AAB22561 and AAB22558); virulence plasmid parA family protein pGP5-D; (Genbank Accession No. Q46263); virulence plasmid protein pGP2-D (Genbank Accession No. Q46260); virulence plasmid protein pGP3-D (Genbank Accession No. Q46261); virulence plasmid protein pGP4-D (Genbank Accession No. Q46262); virulence plasmid protein pGP6-D (Genbank Accession No. Q46264), OmpA (Genbank Accession Nos. AAT36351 and AAT36354) and 60 kDa chaperonin protein (Genbank Accession No. AAT38208).

*C. felis* proteins include heat shock protein GroEL (Genbank Accession Nos. AAL38954 and AAO24106); the major outer membrane protein (Genbank Accession Nos. AAK00238, AAK00239, AAO24108 and CAA43409); MutS (Genbank Accession No. AAD25865); and the outer membrane protein 2 (Genbank Accession Nos. AAK38113, AAK38114, AAK38115, AAL89722, AAO24107, AAQ19779).

In a preferred embodiment, the *Chlamydophila* protein used is an outer membrane protein such as the major outer membrane protein (MOMP). Other suitable *Chlamydophila* proteins include LPS or the OmcB protein.

Typically, the polynucleotide encoding the immunogenic fraction of *C. abortus, C. psittaci* or *C. felis* encodes a structural protein, and more preferably a surface protein, or an immunogenic portion thereof, or a derivative thereof. The nucleic acid sequence encoding the various proteins can readily be ascertained by reference to the above Genbank Accession Nos. and can readily be determined by standard molecular biology techniques.

In an embodiment, the agent capable of raising an immune response against a *Chlamydophila* comprises an inactivated or attenuated *Chlamydophila* having a 218 nucleotide partial sequence of the 23S rRNA gene which has the sequence of SEQ ID NO: 1, or an immunogenic fragment thereof or a derivative thereof, or a nucleic acid encoding said fraction or derivative. A *Chlamydophila* having a 218 nucleotide partial sequence of the 23S rRNA gene which has the sequence of SEQ ID NO: 1 may be found in, and isolated from, the trachea and lungs of dogs with CIRD, typically dogs with CIRD from re-homing centres and boarding or training kennels.

The *Chlamydophila* can be isolated from dogs by inoculating a tissue extract onto a McCoy cell line in the presence or absence of cycloheximide, culturing the cells for up to 10 days at 37° C. with 5% $CO_2$ and then extracting the *Chlamydophila* by freeze-fracturing the cells. This method is routinely used for isolating *Chlamydophilas* from birds, cats, humans, and other hosts. The fragment of the 23S rRNA gene can be amplified from the *Chlamydophila* using the PCR conditions described in Example 3, and the sequence obtained can be verified by comparison to the sequences in FIG. 5 or 8.

For vaccine use, polynucleotide agents can be delivered in various replicating (e.g. recombinant adenovirus vaccine) or non-replicating (DNA vaccine) vectors.

A typical dose of a vaccine comprised of recombinant protein is about 5-10 μg. A typical dose of a bacterial vaccine is $10^8$ colony forming units per ml.

Typically, the vaccine composition further comprises a pharmaceutically acceptable carrier, diluent or adjuvant.

Certain carriers and adjuvants are described above. Other suitable adjuvants include Freund's complete or incomplete adjuvant, muramyl dipeptide, the "Iscoms" of EP 109 942, EP 180 564 and EP 231 039, aluminium hydroxide, saponin, DEAE-dextran, neutral oils (such as miglyol), vegetable oils (such as arachis oil), liposomes, Pluronic® polyols or the Ribi adjuvant system (see, for example GB-A-2 189 141).

The carrier(s) must be "acceptable" in the sense of being compatible with the agent(s) of the invention and not deleterious to the recipients thereof. Typically, the carriers will be water or saline which will be sterile and pyrogen free.

Typically, the vaccine will be administered via the oral, intramuscular, subcutaneous, intravenous, intraperitoneal or intranasal routes.

The vaccine composition may be formulated for parenteral administration, and may include aqueous or non-aqueous sterile injection solutions which may contain anti-oxidants, buffers, bacteriostats and solutes which render the formulation isotonic with the blood of the intended recipient; and/or aqueous or non-aqueous sterile suspensions which may include suspending agents and thickening agents.

The vaccine composition may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets.

The vaccine composition may be formulated for intranasal administration and may be conveniently delivered in the form of an aerosol spray presentation from a pressurised container, pump, spray or nebuliser with the use of a suitable propellant, e.g. dichlorodifluoromethane, trichlorofluoromethane, dichlorotetrafluoro-ethane, a hydrofluoroalkane such as 1,1,1,2-tetrafluoroethane (HFA 134A™ or 1,1,1,2,3,3,3-heptafluoropropane (HFA 227EA™), carbon dioxide or other suitable gas. In the case of a pressurised aerosol, the dosage unit may be determined by providing a valve to deliver a metered amount. The pressurised container, pump, spray or nebuliser may contain a solution or suspension of the agent(s), e.g. using a mixture of ethanol and the propellant as the solvent, which may additionally contain a lubricant, e.g. sorbitan trioleate.

For veterinary use, the vaccine is prepared as an acceptable formulation in accordance with normal veterinary practice and the veterinary surgeon will determine the dosing regimen and route of administration which will be most appropriate for a particular animal.

Formulations for vaccines suitable for administration to dogs are well known in the art and include the formulations used in the dog vaccines described below.

As discussed above, several viral and bacterial agents are known to be associated with respiratory disease in dogs, including canine respiratory coronavirus (CRCV), canine parainfluenza virus (CPIV), canine adenovirus type 2 (CAV-2), canine herpesvirus (CHV), and *Bordetella bronchiseptica* (*B. bronchiseptica*).

Thus, in an embodiment, the vaccine composition further comprises any one or more of:

(d) an agent capable of raising an immune response in a dog against CRCV;

(e) an agent capable of raising an immune response in a dog against CPIV;

(f) an agent capable of raising an immune response in a dog against CAV-2;

(g) an agent capable of raising an immune response in a dog against CHV; and (h) an agent capable of raising an immune response in a dog against *B. bronchiseptica.*

Thus the vaccine composition can optionally also comprise any two, or any three, or any four, or all five of these additional agents.

Typically, an agent capable of raising an immune response in a dog against CRCV comprises inactivated or attenuated CRCV, or an immunogenic fragment of CRCV, or a nucleic acid encoding said immunogenic fraction.

Suitable immunogenic fragments of CRCV are described in WO 2004/011651 (The Royal Veterinary College) and in Erles et al, 2003. Suitable immunogenic fragments of CRCV include the Spike (S) and the hemagglutinin-esterase (HE) surface proteins, the membrane glycoprotein (M), and the nucleocapsid protein (N), or immunogenic portions thereof. The CRCV-like Spike and HE proteins described in WO 2004/011651 may also be suitable as agents that raise an immune response against CRCV. Closely related coronaviruses, such as bovine coronavirus and human coronavirus, and immunogenic fragments thereof, may also be suitable as agents that raise an immune response against CRCV. The entire disclosure of WO 2004/011651 relating to agents that can be used as a vaccine component against CRCV, is incorporated herein by reference.

Typically, an agent capable of raising an immune response in a dog against CPIV comprises inactivated or attenuated CPIV, or an immunogenic fragment thereof, or a nucleic acid encoding said immunogenic fraction.

Typically, an agent capable of raising an immune response in a dog against CAV-2 comprises inactivated or attenuated CAV-2, or an immunogenic fragment thereof, or a nucleic acid encoding said immunogenic fraction.

Canine adenovirus type 1 causes infectious hepatitis; canine adenovirus type 2 causes respiratory disease. It has been shown that CAV-1 provides cross-protection against CAV-2 and vice versa. The agent that raises an immune response in a dog against CAV-2 may therefore contain either CAV-1 or CAV-2, or an immunogenic fragment thereof. The vaccines listed below contain CAV-2 except for EURICAN® DHPPi, which does not specify the virus type used.

Suitable agents that raise an immune response in a dog against CPIV and CAV-2 are known to a person of skill in the art. For example, the following dog vaccines are licensed in the UK.

KAVAK® DA₂PiP69 by Fort Dodge Animal Health is a live freeze dried vaccine containing attenuated strains of canine distemper virus, canine adenovirus type 2, canine parainfluenza type 2 and canine parvovirus grown in tissue culture.

KAVAK® Parainfluenza by Fort Dodge Animal Health contains live freeze-dried vaccine derived from an attenuated strain of canine parainfluenza virus type 2 cultivated on an established homologous cell-line.

NOBIVAC® DHPPi by Intervet UK Limited is a live attenuated freeze-dried, virus vaccine containing canine distemper virus, canine adenovirus type 2, canine parvovirus and canine parainfluenza virus grown in cell line tissue culture.

NOBIVAC® KC by Intervet UK Limited is a modified live freeze-dried vaccine containing *Bordetella bronchiseptica* strain B-C2 and canine parainfluenza virus strain Cornell (this is an intranasal vaccine). Management authorisation number Vm 06376/4026.

EURICAN® DHPPi by Merial Animal Health Ltd. is a combined live freeze-dried vaccine against canine distemper, infectious canine hepatitis, canine parvovirus and canine parainfluenza virus type 2.

VANGUARD® 7 by Pfizer Ltd. contains live attenuated canine distemper virus (Snyder Hill strain), adenovirus (CAV-2 Manhattan strain), parainfluenza virus (NL-CPI-5 strain), canine parvovirus (NL-35-D) propagated in an established cell line, and an inactivated culture of *Leptospira canicola* and *Leptospira icterohaemorrhagiae*.

QUANTUM® DOG 7 by Schering-Plough Animal Health contains canine distemper, adenovirus type 2, parvovirus, parainfluenza virus type 2 vaccine (living) and inactivated *Leptospira canicola* and *Leptospira icterohaemorrhagiae* vaccine.

CANIGEN DHPPi by Virbac Ltd. is a live attenuated, freeze-dried, virus vaccine containing canine distemper virus, canine adenovirus (CAV-2), canine parvovirus and canine parainfluenza virus grown in cell line tissue culture.

CANIGEN Ppi by Virbac Ltd. is a live attenuated, freeze-dried virus vaccine containing canine parvovirus and canine parainfluenza virus grown in cell line tissue culture.

Typically, an agent capable of raising an immune response in a dog against CHV comprises inactivated or attenuated CHV, or an immunogenic fragment thereof, or a nucleic acid encoding said immunogenic fraction.

Suitable agents that raise an immune response in a dog against CHV are known to a person of skill in the art. For example, EURICAN Herpes 205 by Merial is a purified subunit vaccine against CHV which is indicated for the active immunisation of pregnant bitches to prevent mortality, clinical signs and lesions in puppies resulting from CHV infections acquired in the first days of life. It is not licensed for the vaccination of adult dogs for the prevention of respiratory disease.

Typically, an agent capable of raising an immune response in a dog against *B. bronchiseptica* comprises inactivated or attenuated *B. bronchiseptica*, or an immunogenic fragment thereof, or a nucleic acid encoding said immunogenic fraction.

Suitable agents that raise an immune response in a dog against *B. bronchiseptica* are known to a person of skill in the art. For example, the following dog vaccines are licensed for use.

COUGHGUARD-B® by Pfizer Animal Health (U.S. Vet. Lic. No.: 189) contains an inactivated culture of *B. bronchiseptica*. It is for the immunisation of healthy dogs against disease caused by *B. bronchiseptica*, in particular kennel cough. COUGHGUARD-B® is prepared from a highly antigenic strain of *B. bronchiseptica* which has been inactivated and processed to be nontoxic when administered to dogs. The production method is reported to leave the immunogenic properties of *B. bronchiseptica* intact.

VANGUARD® 5/B by Pfizer Animal Health (U.S. Vet. Lic. No.: 189) contains attenuated strains of canine distemper virus (CDV), CAV-2, CPIV, and canine parvovirus (CPV) propagated on an established canine cell line. The CPV antigen was attenuated by low passage on the canine cell line and at that passage level has immunogenic properties capable of overriding maternal antibodies. The vaccine is packaged in lyophilised form with inert gas in place of vacuum. The bacterin component containing inactivated whole cultures of *B. bronchiseptica* which is supplied as diluent. The *B. bronchiseptica* component in VANGUARD® 5/B is prepared from a highly antigenic strain which has been inactivated and processed to be nontoxic when administered to dogs.

NASAGUARD-B™ by Pfizer Animal Health (U.S. Vet. Lic. No.: 112) is composed of an avirulent live culture of *B. bronchiseptica* bacteria.

PROGARD®-KC by Intervet is a modified live intranasal vaccine containing attenuated canine parainfluenza virus and *Bordetella bronchiseptica* avirulent live culture. PROGARD®-KC is presented in a desiccated form with sterile diluent provided for reconstitution. PROGARD®-KC is for vaccination of healthy, susceptible puppies and dogs for prevention of canine infectious tracheobronchitis ("kennel cough") due to canine parainfluenza virus and *B. bronchiseptica*.

PROGARD®-KC PLUS by Intervet contains live culture of avirulent strains of *B. bronchiseptica*, attenuated canine adenovirus type 2 and parainfluenza virus for intranasal administration. Vaccination with PROGARD®-KC Plus stimulates rapid, local immunity in the respiratory tract, thereby inhibiting infection at the port of entry as well as preventing clinical signs. In addition to local immunity, it also stimulates systemic immunity within three weeks of intranasal administration. The small volume (0.4 ml) and one nostril application of PROGARD®-KC Plus provide for ease in vaccination, particularly in small breeds and young puppies. PROGARD®-KC Plus is presented in a desiccated form with sterile diluent provided for reconstitution. PROGARD®-KC Plus is for vaccination of healthy dogs and puppies three weeks of age or older for prevention of canine infectious tracheobronchitis ("kennel cough") due to canine adenovirus type 2, parainfluenza virus and *B. bronchiseptica*.

Intrac by Intervet is a freeze dried modified live vaccine, containing *B. bronchiseptica* strain S 55, for intranasal administration. Product licence number PL 0201/4011

Nobivac® KC, described above, also contains *B. bronchiseptica*.

In an embodiment, the vaccine composition comprises:
(a) an agent capable of raising an immune response in a dog against *S. zooepidemicus*; and/or (b) an agent capable of raising an immune response in a dog against *M. cynos*,
and, optionally, any one or more of:
(c) an agent capable of raising an immune response in a dog against a *Chlamydophila*;
(d) an agent capable of raising an immune response in a dog against CRCV;
(e) an agent capable of raising an immune response in a dog against CPIV;
(f) an agent capable of raising an immune response in a dog against CAV-2;
(g) an agent capable of raising an immune response in a dog against CHV; and
(h) an agent capable of raising an immune response in a dog against *B. bronchiseptica*.

In a preferred embodiment, the vaccine composition comprises:
(b) an agent capable of raising an immune response against *M. cynos* in a dog; and
(d) an agent capable of raising an immune response against CRCV in a dog.

In another preferred embodiment, the vaccine composition comprises:
(b) an agent capable of raising an immune response against *M. cynos* in a dog; and
(d) an agent capable of raising an immune response against CRCV in a dog;
and any one or more of:
(c) an agent capable of raising an immune response in a dog against a *Chlamydophila*;
(e) an agent capable of raising an immune response in a dog against CPIV;
(f) an agent capable of raising an immune response in a dog against CAV-2;
(g) an agent capable of raising an immune response in a dog against CHV; and
(h) an agent capable of raising an immune response in a dog against *B. bronchiseptica*.

It is thus appreciated that as well as agents (b) and (d), the composition may contain any two of agents (c), (e), (f), (g) and (h), or any three or any four of all five of agents (c), (e), (f), (g) and (h).

In another preferred embodiment, the vaccine composition comprises
(a) an agent capable of raising an immune response against *S. zooepidemicus* in a dog; and
(b) an agent capable of raising an immune response against *M. cynos* in a dog; and
(d) an agent capable of raising an immune response against CRCV in a dog;
and any one or more of:
(c) an agent capable of raising an immune response in a dog against a *Chlamydophila*;
(e) an agent capable of raising an immune response in a dog against CPIV;
(f) an agent capable of raising an immune response in a dog against CAV-2;
(g) an agent capable of raising an immune response in a dog against CHV; and
(h) an agent capable of raising an immune response in a dog against *B. bronchiseptica*.

It is thus appreciated that as well as agents (a), (b) and (d), the composition may contain any two of agents (c), (e), (f), (g) and (h), or any three, or any four, of all five of agents (c), (e), (f), (g) and (h).

A second aspect of the invention provides a method of vaccinating a dog against CIRD comprising administering to the dog a vaccine composition according to the first aspect of the invention.

A third aspect of the invention provides a method of treating CIRD in a dog comprising administering to the dog a vaccine composition according to the first aspect of the invention.

Thus it can be seen that the vaccine composition of the first aspect of the invention may be used in combating CIRD whether prophylactically or therapeutically.

A fourth aspect of the invention provides the use of any one or more of:
(a) an agent capable of raising an immune response against *S. zooepidemicus* in a dog;
(b) an agent capable of raising an immune response against *M. cynos* in a dog; and
(c) an agent capable of raising an immune response in a dog against a *Chlamydophila*;
in the preparation of a medicament for prophylaxis or treatment of CIRD in a dog.

In an embodiment, the medicament further comprises any one or more of:
(d) an agent capable of raising an immune response in a dog against CRCV;
(e) an agent capable of raising an immune response in a dog against CPIV;
(f) an agent capable of raising an immune response in a dog against CAV-2;
(g) an agent capable of raising an immune response in a dog against CHV; and
(h) an agent capable of raising an immune response in a dog against *B. bronchiseptica*.

In this and all subsequent aspects of the invention, preferences for (a), (b), (c), (d), (e), (f), (g) and (h) are as described with respect to the first aspect of the invention.

A fifth aspect of the invention provides a method of stimulating an immune response against any one or more of *S. zooepidemicus*, *M. cynos* and a *Chlamydophila* in a dog, the method comprising administering to the dog a respective any one or more of:
(a) an agent capable of raising an immune response against *S. zooepidemicus* in a dog;
(b) an agent capable of raising an immune response against *M. cynos* in a dog; and
(c) an agent capable of raising an immune response in a dog against a *Chlamydophila*;

In an embodiment, the method further comprises administering any one or more of:
(d) an agent capable of raising an immune response in a dog against CRCV;
(e) an agent capable of raising an immune response in a dog against CPIV;
(f) an agent capable of raising an immune response in a dog against CAV-2;
(g) an agent capable of raising an immune response in a dog against CHV; and
(h) an agent capable of raising an immune response in a dog against *B. bronchiseptica*.

A sixth aspect of the invention provides the use of any one or more of:
(a) an agent capable of raising an immune response against *S. zooepidemicus* in a dog;
(b) an agent capable of raising an immune response against *M. cynos* in a dog; and
(c) an agent capable of raising an immune response in a dog against a *Chlamydophila*;

in the preparation of a medicament for stimulating an immune response against said respective any one or more of *S. zooepidemicus, M. cynos* and a *Chlamydophila* in a dog.

In an embodiment, the medicament further comprises any one or more of:
(d) an agent capable of raising an immune response in a dog against CRCV;
(e) an agent capable of raising an immune response in a dog against CPIV;
(f) an agent capable of raising an immune response in a dog against CAV-2;
(g) an agent capable of raising an immune response in a dog against CHV; and
(h) an agent capable of raising an immune response in a dog against *B. bronchiseptica*.

A seventh aspect of the invention provides a composition comprising any one or more of:
(a) an agent capable of raising an immune response against *S. zooepidemicus* in a dog;
(b) an agent capable of raising an immune response against *M. cynos* in a dog; and
(c) an agent capable of raising an immune response in a dog against a *Chlamydophila*,
for use in medicine. Thus the composition is packaged and presented for use in medicine.

It is appreciated that the composition may contain any two of these agents, for example (a) and (b), (a) and (c), or (b) and (c). The composition may contain all three of these agents (a), (b) and (c).

In an embodiment, the composition is for use in veterinary medicine. Thus the composition is packaged and presented for use in veterinary medicine.

Typically, the composition is for use in canine veterinary medicine. Thus the composition is packaged and presented for use in canine veterinary medicine, ie it is packaged and presented for use in dogs.

In an embodiment, the composition further comprises any one or more of:
(d) an agent capable of raising an immune response in a dog against CRCV;
(e) an agent capable of raising an immune response in a dog against CPIV;
(f) an agent capable of raising an immune response in a dog against CAV-2;
(g) an agent capable of raising an immune response in a dog against CHV; and
(h) an agent capable of raising an immune response in a dog against *B. bronchiseptica*.

In an embodiment of this aspect, the composition comprises:
(a) an agent capable of raising an immune response in a dog against *S. zooepidemicus*; and/or
(b) an agent capable of raising an immune response in a dog against *M. cynos*,
and, optionally, any one or more of:
(c) an agent capable of raising an immune response in a dog against a *Chlamydophila*;
(d) an agent capable of raising an immune response in a dog against CRCV;
(e) an agent capable of raising an immune response in a dog against CPIV;
(f) an agent capable of raising an immune response in a dog against CAV-2;
(g) an agent capable of raising an immune response in a dog against CHV; and
(h) an agent capable of raising an immune response in a dog against *B. bronchiseptica*.

In a preferred embodiment of this aspect, the composition comprises:
(b) an agent capable of raising an immune response against *M. cynos* in a dog; and
(d) an agent capable of raising an immune response against CRCV in a dog.

In another preferred embodiment of this aspect, the composition comprises:
(b) an agent capable of raising an immune response against *M. cynos* in a dog; and
(d) an agent capable of raising an immune response against CRCV in a dog;
and any one or more of:
(c) an agent capable of raising an immune response in a dog against a *Chlamydophila;*
(e) an agent capable of raising an immune response in a dog against CPIV;
(f) an agent capable of raising an immune response in a dog against CAV-2;
(g) an agent capable of raising an immune response in a dog against CHV; and
(h) an agent capable of raising an immune response in a dog against *B. bronchiseptica*.

It is thus appreciated that as well as agents (b) and (d), the composition may contain any two of agents (c), (e), (f), (g) and (h), or any three or any four of all five of agents (c), (e), (f), (g) and (h).

In another preferred embodiment of this aspect, the composition comprises
(a) an agent capable of raising an immune response against *S. zooepidemicus* in a dog; and
(b) an agent capable of raising an immune response against *M. cynos* in a dog; and
(d) an agent capable of raising an immune response against CRCV in a dog;
and any one or more of:
(c) an agent capable of raising an immune response in a dog against a *Chlamydophila;*
(e) an agent capable of raising an immune response in a dog against CPIV;
(f) an agent capable of raising an immune response in a dog against CAV-2;
(g) an agent capable of raising an immune response in a dog against CHV; and
(h) an agent capable of raising an immune response in a dog against *B. bronchiseptica*.

It is thus appreciated that as well as agents (a), (b) and (d), the composition may contain any two of agents (c), (e), (f), (g) and (h), or any three, or any four, of all five of agents (c), (e), (f), (g) and (h).

An eighth aspect of the invention provides a kit of parts for the vaccine composition of the first aspect of the invention, comprising any one or more of:
(a) an agent capable of raising an immune response against *S. zooepidemicus* in a dog;
(b) an agent capable of raising an immune response against *M. cynos* in a dog; and
(c) an agent capable of raising an immune response in a dog against a *Chlamydophila*,
and optionally a pharmaceutically acceptable carrier, diluent or adjuvant.

It is appreciated that the kit of parts may contain any two of these agents, for example (a) and (b), (a) and (c) or (b) and (c). The kit may contain all three of these agents (a), (b) and (c).

In an embodiment, the kit further comprises any one or more of:
- (d) an agent capable of raising an immune response in a dog against CRCV;
- (e) an agent capable of raising an immune response in a dog against CPIV;
- (f) an agent capable of raising an immune response in a dog against CAV-2;
- (g) an agent capable of raising an immune response in a dog against CHV; and
- (h) an agent capable of raising an immune response in a dog against *B. bronchiseptica*.

In an embodiment of this aspect, the kit comprises:
- (a) an agent capable of raising an immune response in a dog against *S. zooepidemicus*; and/or
- (b) an agent capable of raising an immune response in a dog against *M. cynos*, and, optionally, any one or more of:
- (c) an agent capable of raising an immune response in a dog against a *Chlamydophila*;
- (d) an agent capable of raising an immune response in a dog against CRCV;
- (e) an agent capable of raising an immune response in a dog against CPIV;
- (f) an agent capable of raising an immune response in a dog against CAV-2;
- (g) an agent capable of raising an immune response in a dog against CHV; and
- (h) an agent capable of raising an immune response in a dog against *B. bronchiseptica*.

In a preferred embodiment of this aspect, the kit comprises:
- (b) an agent capable of raising an immune response against *M. cynos* in a dog; and
- (d) an agent capable of raising an immune response against CRCV in a dog.

In another preferred embodiment of this aspect, the kit comprises:
- (b) an agent capable of raising an immune response against *M. cynos* in a dog; and
- (d) an agent capable of raising an immune response against CRCV in a dog;

and any one or more of:
- (c) an agent capable of raising an immune response in a dog against a *Chlamydophila*;
- (e) an agent capable of raising an immune response in a dog against CPIV;
- (f) an agent capable of raising an immune response in a dog against CAV-2;
- (g) an agent capable of raising an immune response in a dog against CHV; and
- (h) an agent capable of raising an immune response in a dog against *B. bronchiseptica*.

It is thus appreciated that as well as agents (b) and (d), the kit may contain any two of agents (c), (e), (f), (g) and (h), or any three or any four of all five of agents (c), (e), (f), (g) and (h).

In another preferred embodiment of this aspect, the kit comprises:
- (a) an agent capable of raising an immune response against *S. zooepidemicus* in a dog; and
- (b) an agent capable of raising an immune response against *M. cynos* in a dog; and
- (d) an agent capable of raising an immune response against CRCV in a dog;

and any one or more of:
- (c) an agent capable of raising an immune response in a dog against a *Chlamydophila*;
- (e) an agent capable of raising an immune response in a dog against CPIV;
- (f) an agent capable of raising an immune response in a dog against CAV-2;
- (g) an agent capable of raising an immune response in a dog against CHV; and
- (h) an agent capable of raising an immune response in a dog against *B. bronchiseptica*.

It is thus appreciated that as well as agents (a), (b) and (d), the kit may contain any two of agents (c), (e), (f), (g) and (h), or any three, or any four, of all five of agents (c), (e), (f), (g) and (h).

In a ninth aspect, the invention provides a method of making an antibody against any one or more of *S. zooepidemicus*, *M. cynos* or a *Chlamydophila*, comprising raising an immune response to said respective any one or more of *S. zooepidemicus*, *M. cynos* or a *Chlamydophila*, or an immunogenic fragment thereof, in an animal, and preparing an antibody from the animal or from an immortal cell derived therefrom.

Methods and techniques for producing a monoclonal antibody are well known to a person of skill in the art, for example those disclosed in "*Monoclonal Antibodies: A manual of techniques*", H Zola (CRC Press, 1988) and in "*Monoclonal Hybridoma Antibodies: Techniques and Applications*", J G R Hurrell (CRC Press, 1982), incorporated herein by reference.

A tenth aspect of the invention provides a method of obtaining an antibody against any one or more of *S. zooepidemicus*, *M. cynos* or a *Chlamydophila*, comprising selecting an antibody from an antibody-display library using said respective any one or more of *S. zooepidemicus*, *M. cynos* or a *Chlamydophila*, or an immunogenic fragment thereof.

In an embodiment of the ninth and tenth aspects, the *Chlamydophila* is *C. abortus* or *C. psittaci* or *C. felis*. In another embodiment the *Chlamydophila* is *C. muridarum*, *C. pecorum*, *C. pneumoniae*, *C. suis* or *C. trachomatis*.

An eleventh aspect of the invention provides an antibody that specifically binds to *S. zooepidemicus*, *M. cynos* or a *Chlamydophila*. This can be made by the methods of the ninth and tenth aspects of the invention.

In an embodiment, the antibody that specifically binds to a *Chlamydophila* binds to *C. abortus* or *C. psittaci* or *C. felis*. In another embodiment the antibody that specifically binds to a *Chlamydophila* binds to *C. muridarum*, *C. pecorum*, *C. pneumoniae*, *C. suis* or *C. trachomatis*.

In the context of this and subsequent aspects of the invention, by "antibody" we include not only whole immunoglobulin molecules but also fragments thereof such as Fab, F(ab'$_2$, Fv and other fragments thereof that retain the antigen-binding site. Similarly in these contexts, the term "antibody" includes genetically engineered derivatives of antibodies such as single chain Fv molecules (scFv) and domain antibodies (dAbs). The term also includes antibody-like molecules which may be produced using phage-display techniques or other random selection techniques for molecules which bind to the particular organism or to regions of the particular organism. Thus, in these contexts, the term antibody includes all molecules which contain a structure, preferably a peptide structure, which is part of the recognition site (ie the part of the antibody that binds or combines with the epitope or antigen) of a natural antibody.

The variable heavy ($V_H$) and variable light ($V_L$) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parented antibody (Morrison et al (1984) *Proc. Natl. Acad. Sci. USA* 81, 6851-6855).

That antigenic specificity is conferred by variable domains and is independent of the constant domains is known from experiments involving the bacterial expression of antibody fragments, all containing one or more variable domains. These molecules include Fab-like molecules (Better et al (1988) *Science* 240, 1041); Fv molecules (Skerra et al (1988) *Science* 240, 1038); single-chain Fv (ScFv) molecules where the $V_H$ and $V_L$ partner domains are linked via a flexible oligopeptide (Bird et al (1988) *Science* 242, 423; Huston et al (1988) *Proc. Natl. Acad. Sci. USA* 85, 5879) and single domain antibodies (dAbs) comprising isolated V domains (Ward et al (1989) *Nature* 341, 544). A general review of the techniques involved in the synthesis of antibody fragments which retain their specific binding sites is to be found in Winter & Milstein (1991) *Nature* 349, 293-299.

By "ScFv molecules" we mean molecules wherein the $V_H$ and $V_L$ partner domains are linked via a flexible oligopeptide. Engineered antibodies, such as ScFv antibodies, can be made using the techniques and approaches described in J. Huston et al, (1988) "Protein engineering of antibody binding sites: recovery of specific activity in an anti-digoxin single chain Fv analogue produced in *E. coli*", *Proc. Natl. Acad. Sci. USA*, 85, pp. 5879-5883, and in A. Pluckthun, (June 1991) "Antibody engineering; Advances from use of *E. coli* expression systems", *Bio/technology* vol 9, incorporated herein by reference.

The advantages of using antibody fragments, rather than whole antibodies, are several-fold. The smaller size of the fragments may lead to improved pharmacological properties, such as better penetration to the target site. Effector functions of whole antibodies, such as complement binding, are removed. Fab, Fv, ScFv and dAb antibody fragments can all be expressed in and secreted from *E. coli*, thus allowing the facile production of large amounts of the fragments.

Whole antibodies, and F(ab')$_2$ fragments are "bivalent". By "bivalent" we mean that the antibodies and F(ab')$_2$ fragments have two antigen combining sites. In contrast, Fab, Fv, ScFv and dAb fragments are monovalent, having only one antigen combining site.

Although the antibody may be a polyclonal antibody, it is preferred if it is a monoclonal antibody. In some circumstance, particularly if the antibody is going to be administered repeatedly to a dog, it is preferred if the monoclonal antibody is a dog monoclonal antibody or a "caninised" antibody.

Polyclonal antibodies may be produced which are polyspecific or monospecific. It is preferred that they are monospecific. Chimaeric antibodies are discussed by Neuberger et al (1998, 8$^{th}$ *International Biotechnology Symposium* Part 2, 792-799).

It is preferred if the antibody is a "caninised" antibody. Suitably prepared non-dog antibodies can be "caninised" in known ways, for example by inserting the CDR regions of mouse antibodies into the framework of dog antibodies. Caninised antibodies can be made using techniques and approaches corresponding to those described for humanisation of antibodies in M. Verhoeyen, C. Milstein and G. Winter (1988) "Reshaping human antibodies: Grafting an antilysozyme activity", *Science*, 239, 1534-1536, and in C. Kettleborough et al., (1991) "Humanisation of a mouse monoclonal antibody by CDR grafting; The importance of framework residues in loop conformation", *Protein Engineering*, 14(7), 773-783, incorporated herein by reference.

It is appreciated that a dog can passively acquire immunity against CIRD by being administered an antibody that reacts with an agent that is involved in the disease.

Thus, a twelfth aspect of the invention provides a method of passively immunising a dog against CIRD comprising administering to the dog one or more antibodies that specifically bind to a respective one or more of *S. zooepidemicus, M. cynos*, and a *Chlamydophila*.

The antibodies that specifically bind to the *S. zooepidemicus, M. cynos*, and the *Chlamydophila* may be made or obtained using standard techniques such as those described above.

It is appreciated that CIRD in a dog may be treated by administering an antibody that reacts with an agent that is involved in the disease.

In a thirteenth aspect, the invention provides a method of treating CIRD in a dog comprising administering to the dog one or more antibodies that specifically bind to a respective one or more of *S. zooepidemicus, M. cynos*, and a *Chlamydophila*.

In an embodiment of the twelfth or thirteenth aspects, the antibody that specifically binds to the *Chlamydophila* binds to *C. abortus*, or *C. psittaci* or *C. felis*. In another embodiment the antibody that specifically binds to the *Chlamydophila* binds to *C. muridarum, C. pecorum, C. pneumoniae, C. suis* or *C. trachomatis*.

In an embodiment of the twelfth or thirteenth aspects, the method further comprises administering antibodies that specifically bind to any one or more of CRCV, CPIV, CAV-2, CHV, and *B. bronchiseptica*.

The antibodies that specifically bind to CRCV, CPIV, CAV-2, CHV, and *B. bronchiseptica* can be made using standard techniques such as those described above.

A fourteenth aspect of the invention provides the use of one or more antibodies that specifically bind to a respective one or more of *S. zooepidemicus, M. cynos*, and a *Chlamydophila*, in the preparation of a medicament for passively immunising a dog against CIRD.

A fifteenth aspect of the invention provides the use of one or more antibodies that specifically bind to a respective one or more of *S. zooepidemicus, M. cynos*, and a *Chlamydophila*, in the preparation of a medicament for treating CIRD in a dog.

In an embodiment of the fourteenth or fifteenth aspects, the antibody that specifically binds to the *Chlamydophila* binds to *C. abortus*, or *C. psittaci* or *C. felis*. In another embodiment the antibody that specifically binds to the *Chlamydophila* binds to *C. muridarum, C. pecorum, C. pneumoniae, C. suis* or *C. trachomatis*.

In an embodiment of the fourteenth or fifteenth aspects, the medicament further comprises antibodies that specifically bind to any one or more of CRCV, CPIV, CAV-2, CHV, and *B. bronchiseptica*.

A sixteenth aspect of the invention provides a composition comprising any two or more of an antibody that specifically binds to *S. zooepidemicus*, an antibody that specifically binds to *M. cynos*, and an antibody that specifically binds to a *Chlamydophila*.

In an embodiment, the antibody that specifically binds to the *Chlamydophila* binds to *C. abortus*, or *C. psittaci* or *C. felis*. In another embodiment the antibody that specifically binds to the *Chlamydophila* binds to *C. muridarum, C. pecorum, C. pneumoniae, C. suis* or *C. trachomatis*.

In an embodiment, the composition further comprises antibodies that specifically bind to any one or more of CRCV, CPIV, CAV-2, CHV, and *B. bronchiseptica*.

It will also be appreciated that the invention includes diagnostic methods and assays. Thus, the invention provides a method of determining whether a dog has been exposed to a *Chlamydophila* species associated with CIRD, the method comprising:
(a) obtaining a suitable sample from the dog; and
(b) identifying a *Chlamydophila* species associated with CIRD, or an antibody there to, in the sample.

Typically, the *Chlamydophila* species is one which has a 23S RNA comprising the sequence (when shown as RNA) of any of SEQ ID Nos: 1 to 8 (see FIGS. 5 and 8 which show partial 23S RNA sequences, and Example 3).

The invention also provides a method of determining whether a dog has or is susceptible to CIRD, the method comprising:
(a) obtaining a suitable sample from the dog; and
(b) identifying any one or more of *S. zooepidemicus* or *M. cynos* or *Chlamydophila*, or an antibody to any of these, in the sample.

It will be appreciated that the methods can detect, in one embodiment, present exposure to the organism for example by detecting the organism itself or a component thereof (such as protein or nucleic acid) within the sample. The methods can also detect past exposure to the organism by detecting antibodies in the sample which are directed at the organism or to components thereof.

Typically, the sample is any suitable sample, including antibody containing samples such as serum, saliva, tracheal wash and bronchiolar lavage.

The presence of the organism in the dog from which the sample is derived may therefore be determined by analysing the sample for the presence of the organism or component thereof. For example, for nucleic acid components, including 23S RNA, nucleic acid is extracted and may be copied into DNA if necessary, and detected, for example, using techniques involving high stringency hybridisation, specific amplication, nucleotide sequencing and other methods well known to the person skilled in the art (Sambrook et al (2001) supra). By "hybridising at high stringency" is meant that the polynucleotide and the nucleic acid to which it hybridises have sufficient nucleotide sequence similarity that they can hybridise under highly stringent conditions. As is well known in the art, the stringency of nucleic acid hybridisation depends on factors such as length of nucleic acid over which hybridisation occurs, degree of identity of the hybridising sequences and on factors such as temperature, ionic strength and CG or AT content of the sequence.

Nucleic acids which can hybridise at high stringency to nucleic acid molecules of the organism include nucleic acids which have >90% sequence identity, preferably those with >95% or >96% or >97% or >98, more preferably those with >99% sequence identity, over at least a portion of the nucleic acid of the organism.

Typical highly stringent hybridisation conditions which lead to selective hybridisation are known in the art, for example those described in Sambrook et al 2001 (supra), incorporated herein by reference.

An example of a typical hybridisation solution when a nucleic acid is immobilised on a nylon membrane and the probe nucleic acid is ≧500 bases is:
6×SSC (saline sodium citrate)
0.5% sodium dodecyl sulphate (SDS)
100 μg/ml denatured, fragmented salmon sperm DNA The hybridisation is performed at 68° C. The nylon membrane, with the nucleic acid immobilised, may be washed at 68° C. in 0.1×SSC.

20×SSC may be prepared in the following way. Dissolve 175.3 g of NaCl and 88.2 g of sodium citrate in 800 ml of $H_2O$. Adjust the pH to 7.0 with a few drops of a 10 N solution of NaOH. Adjust the volume to 1 liter with $H_2O$. Dispense into aliquots. Sterilise by autoclaving.

An example of a typical hybridisation solution when a nucleic acid is immobilised on a nylon membrane and the probe is an oligonucleotide of between 15 and 50 bases is:
3.0 M trimethylammonium chloride (TMACl)
0.01 M sodium phosphate (pH 6.8)
1 mm EDTA (pH 7.6)
0.5% SDS
100 μg/ml denatured, fragmented salmon sperm DNA
0.1% non-fat dried milk The optimal temperature for hybridisation is usually chosen to be 5° C. below the $T_i$ for the given chain length. $T_i$ is the irreversible melting temperature of the hybrid formed between the probe and its target sequence. Jacobs et al (1988) *Nucl. Acids Res.* 16, 4637 discusses the determination of $T_i$s. The recommended hybridization temperature for 17-mers in 3M TMACl is 48-50° C.; for 19-mers, it is 55-57° C.; and for 20-mers, it is 58-66° C.

Assaying a protein component of the organism in a sample from the dog can be done using any method known in the art. Typically, such methods are antibody bound, and the antibody binds to the organism or a component thereof.

For example, expression of protein from the organism can be studied with classical immunohistological methods. In these, the specific recognition is provided by the primary antibody (polyclonal or monoclonal) but the secondary detection system can utilise fluorescent, enzyme, or other conjugated secondary antibodies. As a result, an immunohistological staining of tissue section for pathological examination is obtained. Tissues can also be extracted, e.g., with urea and neutral detergent, for the liberation of protein for Western-blot or dot/slot assay (Jalkanen, M., et al, *J. Cell. Biol.* 101: 976-985 (1985); Jalkanen, M., et al, *J. Cell. Biol.* 105:3087-3096 (1987)). In this technique, which is based on the use of cationic solid phases, quantitation of protein can be accomplished using isolated protein as a standard. This technique can also be applied to body fluid samples.

Other antibody-based methods useful for detecting protein expression include immunoassays, such as the enzyme linked immunosorbent assay (ELISA) and the radioimmunoassay (RIA). For example, a reactive monoclonal antibody can be used both as an immunoadsorbent and as an enzyme-labeled probe to detect and quantify the protein. The amount of protein present in the sample can be calculated by reference to the amount present in a standard preparation using a linear regression computer algorithm. Such an ELISA for detecting a tumour antigen is described in Iacobelli et al, *Breast Cancer Research and Treatment* 11: 19-30 (1988). In another ELISA assay, two distinct specific monoclonal antibodies can be used to detect protein in a body fluid. In this assay, one of the antibodies is used as the immunoadsorbent and the other as the enzyme-labeled probe.

The above techniques may be conducted essentially as a "one-step" or "two-step" assay. The "one-step" assay involves contacting protein with immobilized antibody and, without washing, contacting the mixture with the labeled antibody. The "two-step" assay involves washing before contacting the mixture with the labeled antibody. Other conventional methods may also be employed as suitable. It is usually desirable to immobilize one component of the assay system on a support, thereby allowing other components of the system to be brought into contact with the component and readily removed from the sample.

Suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labeled antibody/substrate reaction. Besides enzymes, other suitable labels include radioisotopes, such as iodine ($^{125}$I, $^{121}$I), carbon ($^{14}$C), sulfur ($^{35}$S), tritium ($^{3}$H), indium ($^{112}$In), and technetium ($^{99}$mTc), and fluorescent labels, such as fluorescein and rhodamine, and biotin.

Antibodies to the organism or component thereof may be detected using, for example, the well known technique of immunosorbent assay, such as an enzyme linked immunosorbent assay (ELISA).

Thus, a further aspect of the invention provides an immunosorbent assay for detecting antibodies associated with CIRD, the assay comprising: a solid phase coated with any one or more of (a) an agent capable of raising an immune response against *S. zooepidemicus* in a dog; (b) an agent capable of raising an immune response against *M. cynos* in a dog; and (c) an agent capable of raising an immune response against a *Chlamydophila* in a dog; and a detectable label conjugate which will bind to the antibodies bound to the solid phase.

Preferably, the solid phase is a microtitre well. Further preferably, the conjugate comprises anti-dog antibody antibody. Preferably, the conjugate comprises an enzyme, for example horseradish peroxidase. Further preferably, the immunosorbent assay also comprises a substrate for the enzyme. The invention includes a kit of parts which include the components of the immunosorbent assay. The kit of parts may thus include a solid phase such as a microtitre plate, protein from the organism or organisms for coating the solid phase, a detectable label conjugate, such as an anti-dog antibody, which will bind to anti-organism (or component thereof) antibodies bound to the solid phase. If the detectable label conjugate is an enzyme, the kit of parts may also include a substrate for the enzyme. The kit may also include a positive control sample that contains an antibody known to react with the antigen on the solid substrate, and a negative control sample.

The invention also includes a solid phase substrate coated with any one or two or all three of (a), (b) and (c) as defined above and in the first aspect of the invention. Typically, the agent which is capable of raising an immune response is one which will also bind an antibody. Typically, the agent is an antigenic protein. Typically, protein is coated on microtitre plates overnight at 4° C. to 37° C., depending on the stability of the antigen. Unbound protein is washed off with a wash buffer such as phosphate buffered saline or Tris buffered saline. Serum or other samples are incubated on the plate, typically at 37° C. for between 1 and several hours. Unbound material is washed off, the plates are incubated with enzyme-labelled (eg horseradish peroxidase) antibody, such as anti-canine IgG or IgM for serum samples, or anti-canine IgA for lung washes, for 1 to several hours at 37° C. Unbound antibody is washed off and plates are incubated with a substrate such as OPD for about 10 min, and the optical density measured in a photometer.

Preferably, the solid substrate is a microtitre well.

All of the documents referred to herein are incorporated herein, in their entirety, by reference. The listing or discussion of a prior-published document in this specification should not necessarily be taken as an acknowledgement that the document is part of the state of the art or is common general knowledge.

The invention will now be described in more detail with the aid of the following Figures and Examples.

BRIEF DESCRIPTION OF THE DRAWINGS

FIG. 5: 218 partial nucleotide sequence (SEQ ID NO: 1) of the 23S rRNA gene from a *Chlamydophila* isolated from a dog with CIRD (DHB10).

FIG. 8: 218 partial nucleotide sequences (SEQ ID NOs: 2-8) of the 23S rRNA gene from seven further isolates of a *Chlamydophila* species isolated from a dog with CIRD (DHB 2, 4, 5, 6, 7, 8 and 9).

DETAILED DESCRIPTION OF THE PREFERRED EMBODIMENT

Example 1

Figure 1:
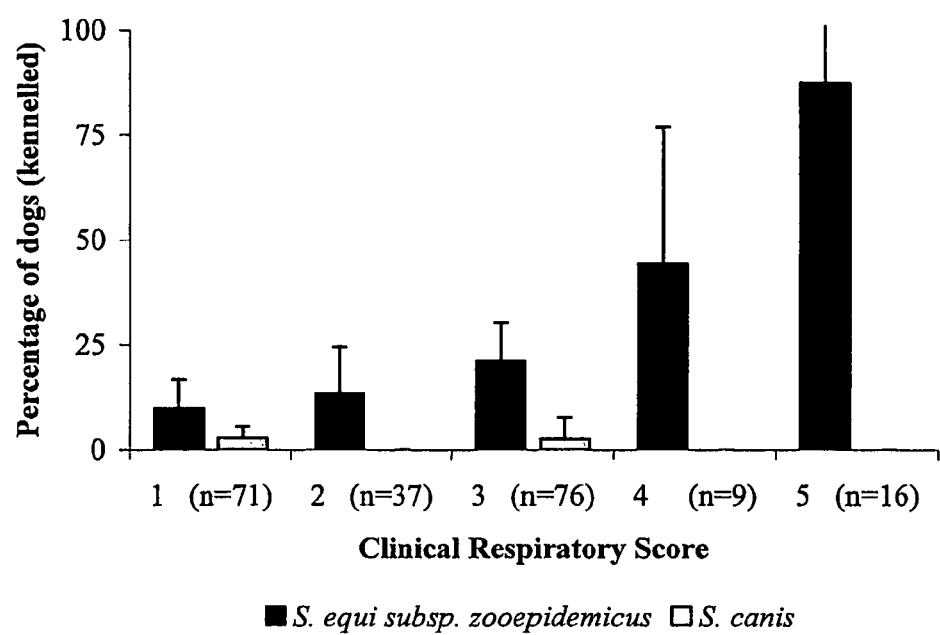
FIG. 1: Isolation of *S. canis* and *S. zooepidemicus* from 209 kennelled dogs with clinical respiratory score (n=total number of dogs in each group). Error bars represent confidence intervals (95%).

The Association of *Streptococcus equi* Sub Species *zooepidemicus* with Canine Infectious Respiratory Disease Summary Canine infectious respiratory disease (CIRD) is a multifactorial infection that affects many kennelled dogs despite the wide use of vaccination. Current vaccines aim to protect against viral agents and a single bacterial agent, *Bordetella bronchiseptica*. We examined the role of streptococcal species in CIRD. The isolation and identification of streptococci in the lower respiratory tract of clinically healthy dogs and those with CIRD were used to correlate the presence of specific streptococcal species with respiratory disease. We show that the presence of *S. equi* sub species *zooepidemicus* (*S. zooepidemicus*) is associated with increasing severity of disease in a population of kennelled dogs with endemic CIRD.

Introduction

CIRD is an infection that affects dogs of all ages and commonly occurs when large numbers of dogs are housed together in close confinement. The disease has high morbidity with the dry hacking cough characteristic of laryngitis in the early stages, nasal and/or ocular discharges, and variable anorexia and depression, which can progress to tracheobronchitis, pneumonia and even death in more severe cases. The disease has historically been regarded as a complex infection in which combined or sequential challenge with both viral (CPIV and CAV-2) and bacterial agents produces a synergistic enhancement of the clinical scores (Appel and Binn, 1987). The most common bacterial agent detected during the disease is *B. bronchiseptica* (McCandlish et al, 1978), but other bacterial species such as *Pasteurella* sp, *Mycoplasma* sp. and β-haemolytic streptococci (βhS) have all been associated with disease (McCandlish et al, 1978; Rosendal, 1978; Thrusfield et al, 1991).

Many studies involving bacterial isolation from the upper (oral and nasal cavity) and lower respiratory tract (trachea and lungs) of both diseased and healthy dogs mention the presence of βhS (Smith, 1967; McCandlish et al, 1978; McKiernan et al, 1982; Azetaka and Konishi, 1988). However, despite the variety of species of βhS found in the upper respiratory tract of dogs, only a few investigations have focused upon the species of βhS involved in lower airway disease (Garnett et al, 1982; Angus et al, 1997). Although species of βhS in the canine respiratory tract were noted by Biberstein et al, (1980) this study neglected to distinguish between carriage in the upper and lower respiratory tract. Furthermore, even though isolation was from veterinary hospital patients the reason for referral and therefore any link to specific clinical conditions was omitted. The most common βhS in dogs, *S. canis*, a Lancefield Group G *Streptococcus*, is a normal commensal of the genital and respiratory mucosa as well as skin (Timoney, 1987; Quinn et al, 1999). *Streptococcus canis* (*S. canis*) has previously been isolated from the tonsils of 60 to 73% of healthy dogs (Smith, 1967; Sadatsune and Moreno, 1975; Biberstein and Hirsh, 1999). *S. canis* causes a variety of sporadic and opportunistic infections in dogs, including pneumonia, septicemia, abscesses, otitis, mastitis, pyometra, proctitis, toxic shock syndrome and necrotising fasciitis (Biberstein and Hirsh, 1999; Quinn et al, 1999).

In addition to *S. canis* βhS of other Lancefield Groups, such as A, C and E, have also been isolated from dogs (Biberstein et al, 1980). *S. zooepidemicus*, Lancefield Group C, is found as a commensal of the upper respiratory tract mucosa of mammals (Timoney et al, 1988; Quinn et al, 1999). It is associated with several disease syndromes including lower airway disease, foal pneumonia and cervicitis in horses (Chanter, 1997; Biberstein and Hirsh, 1999), pneumonia in llamas (Biberstein and Hirsh, 1999), septicaemia and arthritis in pigs (Timoney, 1987), mastitis in cows and goats (Timoney et al, 1988), septicaemia in poultry, pericarditis and pneumonia in lambs (Timoney, 1987), lymphadenitis in guinea pigs (Quinn et al, 1999) and glomerulonephritis in humans (Balter et al, 2000). In dogs *S. zooepidemicus* has been associated with wound infections, septicaemia (Quinn et al, 1999) and acute necrotising haemorrhagic pneumonia (Garnett et al, 1982). In this study we sought to establish which species of βhS are present in the respiratory tract of both healthy dogs and those with CIRD.

Materials & Methods

Study Populations and Sampling.

The main study population (n=209, bronchial alveolar lavage, BAL) comprised animals from a well-established re-homing kennel (~600 dogs) with a history of endemic CIRD. On entry to the kennel all dogs were vaccinated with KAVAK DA$_2$ PiP69 (Fort Dodge) a live attenuated vaccine for distemper virus, CAV-2, CPIV and canine parvovirus and KAVAK L against Leptospirosis. The presence of both canine coronavirus (CRCV) and *B. bronchiseptica* has been demonstrated in dogs with CIRD in this centre (Chalker et al, 2003; Erles et al, 2003). Each week this kennel must sacrifice some dogs for welfare reasons and from these dogs 2-3 were selected arbitrarily for sampling. BAL samples were taken by the following method from a total of 209 individual dogs over a 2 year period from 1999 to 2001. Within 2 hours of euthanasia the trachea was clamped just above the bifurcation to prevent any tracheal contamination of the lung during sampling. Using sterile catheter tubing 50 ml Hanks Balanced Salt solution was then placed into the left apical lung lobe. This lung lobe was then massaged manually for 30 seconds and the BAL withdrawn. At euthanasia dogs were also graded for the severity of clinical respiratory score into the following categories: (1) No respiratory signs, n=71 (2) Mild cough, n=37 (3) Cough and nasal discharge, n=76 (4) Cough and nasal discharge with depression and/or inappetence n=9 (5) suppurative bronchopneumonia, n=16.

After BAL sampling a section of lung tissue from the right distal lobe was taken for histological analysis. Formalin fixed (10% formalin saline) tissue blocks were embedded in paraffin, and standard haemtoxylin and eosin stained sections were viewed under a light microscope (×40, ×100, ×400). The presence or absence of intra-alveolar neutrophils was noted.

The total number of days each dog spent in the kennel was recorded and time in the kennel was then calculated in weeks. The age and clinical condition on entry into the kennel of each animal was noted and a clinical condition composite score based on nutritional status, coat, demeanour, appetite and a general clinical examination (temperature, pulse rate, respiration rate) was graded as follows: good (1), poor (2), very poor (3).

An additional dog population was included as a control group that comprised of household pet dogs with clinical respiratory symptoms referred to diagnostic bacteriology at the RVC over a 2 year period (1998 to 2000) (n=71, BAL). Samples from the control group were collected using an endoscopically guided technique as described by Cocoran (1998). All samples in the study were kept at 4° C. until bacteriological testing, and testing was performed within 24 h of sampling excepting the calculation of CFU per ml that was performed on frozen BAL.

Bacterial Isolation and Identification.

A 50 μl volume of BAL was plated in duplicate onto Columbia Blood Agar (Oxoid Ltd., Hampshire, UK) plates with 5% sterile sheep blood, and incubated both aerobically and anaerobically for 24 hrs at 37° C. β-haemolytic colonies were identified and then purified to single colonies. Gram-positive catalase-negative bacteria were identified as streptococci by colonial and cellular morphology, and then sero-grouped by latex bead slide agglutination (Oxoid Ltd., Hampshire, UK) into Lancefield Groups. Isolates were then identified to the species level by biochemical utilisation and enzymatic action using the API20STREP manual identification kit (bioMérieux UK Ltd., Basingstoke, UK).

In order to detect mixed infections 3 colonies from the first 12 dogs in the study were tested by both latex bead slide agglutination and API20STREP. Serial dilutions of BAL in phosphate buffered saline (Sigma-Aldrich Co. Ltd., Dorset, UK) were plated in triplicate, incubated as described above and the CFU per ml BAL calculated. Growth of βhS was then graded as follows: none (0), <100 CFU per ml (1), 100 to 1000 CFU per ml (2), and >1000 CFU per ml (3).

Statistical Analyses

A significance level or probability of a type I error (α) of 0.05 was assumed for all analyses. The presence of *S. zooepidemicus* with the age, clinical condition on entry to the kennel, weeks in the kennel, the presence of intra-alveolar neutrophils and clinical respiratory scores was analysed using Prism (version 3.0, GrapbPad Software Inc, San Diego, USA) statistical analysis software $\chi^2$ testing. The correlation of bacterial growth and respiratory score was determined by use of the combined mean scores for *S. zooepidemicus* growth for each respiratory score, analysed with Prism one way ANOVA (non-parametric) testing. The presence of *S. canis, S. zooepidemicus* and respiratory disease in the sampled kennelled dogs with time in weeks was also calculated.

Results

β-haemolytic streptococci were isolated from both study populations, and isolation from the BAL of household pets was markedly different from the kennelled dogs (1.4% household, 23.9% kennel, $\chi^2$ analysis ***p=0.000). All hS isolates were found to be *S. canis* or *S. zooepidemicus*. Mixed infections with differing Lancefield Groups or species were not found, furthermore all individual plates yielded colonies of uniform morphology. Both *S. canis* and *S. zooepidemicus* were isolated from the kennelled dogs, whereas only a single isolate of *S. zooepidemicus* and no *S. canis* were isolated from the household pets. *S. zooepidemicus* was found to be the predominant hS species in the kennelled dogs (92.0%). The carriage of both *S. canis* and *S. zooepidemicus* was examined in the kennelled dogs within each grade of clinical respiratory score (FIG. 1). *S. canis* was present in dogs both with and without clinical scores, and isolation did not increase with disease severity. By contrast, healthy dogs were less likely to have *S. zooepidemicus* in the lower respiratory tract than diseased animals ($\chi^2$ analysis, **p=0.004) and the isolation of *S. zooepidemicus* increased dramatically with increasing clinical respiratory score, from 9.7% in dogs with no symptoms to 87.5% in those dogs with suppurative bronchopneumonia ($\chi^2$ analysis, ***p=0.000). Dogs with higher respiratory scores were also more likely to have a greater mean *S. zooepidemicus* bacterial growth score than clinically healthy dogs (one way ANOVA analysis ***p=0.000. R squared=0.194, F=22.265). The age and clinical condition of the animal on entry to the kennel had no affect on the isolation of *S. zooepidemicus* ($\chi^2$ analysis, age p=0.341, clinical condition on entry p=0.295).

Figure 2:
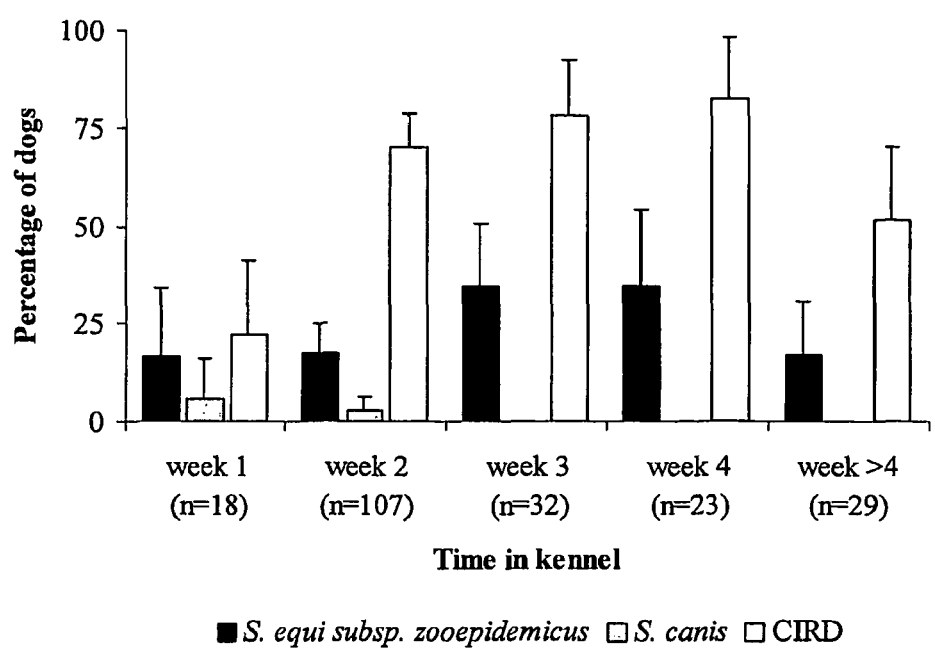
FIG. 2: Percentage of dogs with CIRD, *S. canis* or *S. zooepidemicus* with time in the kennel (n=total number of dogs in each group from a total of 209 dogs). Error bars represent confidence intervals (95%).

The percentage of dogs with CIRD in the kennel increased dramatically from 21.1% in week 1 to 70.1% in week 2, and CIRD did not decrease in the population until after the fourth week (FIG. 2). Although no significant difference was detected, the number of dogs with *S. zooepidemicus* in the lung increased by 20.6% with time in the kennel from 16.7% in week 1 to 34.4% in week 3 (FIG. 2), whereas no such trend was seen with *S. canis*.

Histological analysis revealed that dogs with *S. zooepidemicus* were more likely to have intra-alveolar neutrophils than those without *S. zooepidemicus* ($\chi^2$ analysis, **p=0.006). In dogs with higher bacterial scores, acute suppurative or necrotizing pneumonia with moderate to marked macrophage aggregation was often noted, similar to the findings of Garnett et al, (1982) in dogs with *S. zooepidemicus* induced haemorrhagic streptococcal pneumonia (HSP). No bacterial cells were apparent on H and E stained sections.

Discussion

In this study we focused upon the species of βhS present in the lower respiratory tract of household and kennelled dogs, with and without respiratory disease. Although *S. canis* is the predominant βhS of the respiratory tract in dogs (Biberstein et al, 1980) and was isolated from the lower respiratory tract of some kennelled dogs in this study, it was not associated with CIRD in the kennelled dogs. In contrast, an increased isolation of *S. zooepidemicus* was associated with increasing CIRD severity. Dogs with any respiratory symptoms were more likely to have *S. zooepidemicus* in the lower respiratory tract than more healthy animals in the kennel and *S. zooepidemicus* was found in a lower proportion of the household pets than the kennelled dogs.

*Streptococcus equi* sub species *zooepidemicus* has previously been associated with HSP in dogs (Garnett et al, 1982). The HSP syndrome was a severe infection in a closed colony of beagles, in which sudden death ensued without prior clinical scores. Necropsy findings included abundant haemorrhagic exudates within the trachea and bronchial tree, with diffuse dark reddening of the lungs. In addition, there were ecchymotic haemorrhages of a range of other tissues. The disease was reproduced by intra-tracheal inoculation with *S. zooepidemicus* in one dog. Interestingly in this study, dogs with higher *S. zooepidemicus* growth scores were more likely to have intra-alveolar neutrophils and share histological features of the lungs described by Garnett et al, (1982) in HSP than those dogs with low growth scores.

CIRD has historically been considered a complex disease, involving both bacterial and viral agents. Indeed, several other agents have been described in this kennelled population of dogs, including CRCV (Erles et al, 2003) and *B. bronchiseptica* (Chalker et al, 2003). Although the pathogenic potential of CRCV has not yet been clarified, data by Erles et al (2003) shows that CRCV predominates in those dogs with mild respiratory disease (score 2) and similarly Chalker et al (2003) found that dogs with *B. bronchiseptica* predominates in those dogs with moderate disease (score 3).

We found that *Streptococcus zooepidemicus* is associated more commonly with only the more severe cases of CIRD (score 4-5) indicating it may act as a secondary invader. Indeed, βhS species have previously been described as secondary invaders in the CIRD 'complex' (McCandlish et al, 1978). However, it is still not known if *S. zooepidemicus* plays a primary role in respiratory disease in these animals or merely invades the respiratory tract following damage by other pathogens. Epidemiological evidence suggests that in the horse *S. zooepidemicus* may be a primary pathogen in respiratory disease (Wood et al, 1993; Chanter, 1997) but it is generally considered to be an opportunistic pathogen (Walker and Timoney 1998; Anzai et al, 2000). Even if *S. zooepidemicus* is not a primary cause of CIRD in these dogs, the high isolation rate from dogs with suppurative bronchopneumonia (87.5%) supports the hypothesis that *S. zooepidemicus* is responsible for the more severe clinical signs seen in this kennel. The low isolation from household pets (1.4%) with respiratory disease indicates this agent may not be a common respiratory infection and could be a problem particular to this kennel. Although any previous kennelling was not taken into consideration it is likely that some of the household pet dogs in this study have been kennelled at one time. The role played by *S. zooepidemicus* in other cases of CIRD in kennelled dogs has not been ascertained.

The isolation of *S. zooepidemicus* from these dogs increases with time in the kennel, indicating the lungs of these dogs are becoming infected with this bacterium. Such infection could be occurring from either sub-clinical infections of the upper respiratory tract or from a single pathogenic strain. A PCR typing system for the gene of the variable M-like SzP protein enables the separation of the 15 known sero-types of *S. zooepidemicus* into five distinct groups, *HV*1-5 (Walker and Timoney, 1998). Analyses with this typing system by Anzai et al, (2000) found that single clonal variants of *S. zooepidemicus* are found in the pneumonic equine lung whereas several types are found in the tonsils of healthy horses. It would be of interest to sub-type the *S. zooepi-* demicus isolates involved in this outbreak of CIRD to determine whether a single clonal variant is present in the diseased population, and also to examine the relationship, if any, that canine *S. zooepidemicus* isolates have to those causing respiratory disease in horses and other animals. *S. zooepidemicus* associated pneumonia occurs in horses of all ages and acute haemorrhagic pneumonia in older horses that have been stressed by transportation (Anzai et al, 2000). In this outbreak of CIRD younger dogs and those in poor clinical condition on entry to the kennel were equally susceptible to infection with *S. zooepidemicus* as the older dogs and those that were healthy on entry.

In this kennel antibiotic therapy is given for a range of infections, and treatment is not routinely given to dogs with CIRD except in cases of severe bronchopneumonia. It is possible that treatment could have influenced the bacterial spectrum noted in this study. However the examination of natural outbreaks of respiratory disease can provide valuable information that cannot be obtained by other means.

CIRD is known to be a multi-factorial disease involving several agents including CAV-2, CPIV, *B. bronchiseptica* and *Mycoplasma* spp. In this kennel in which large numbers of dogs from a variety of locations are brought together and housed, several pathogens are present and the severity of the disease may reflect this.

Example 2

Figure 3:
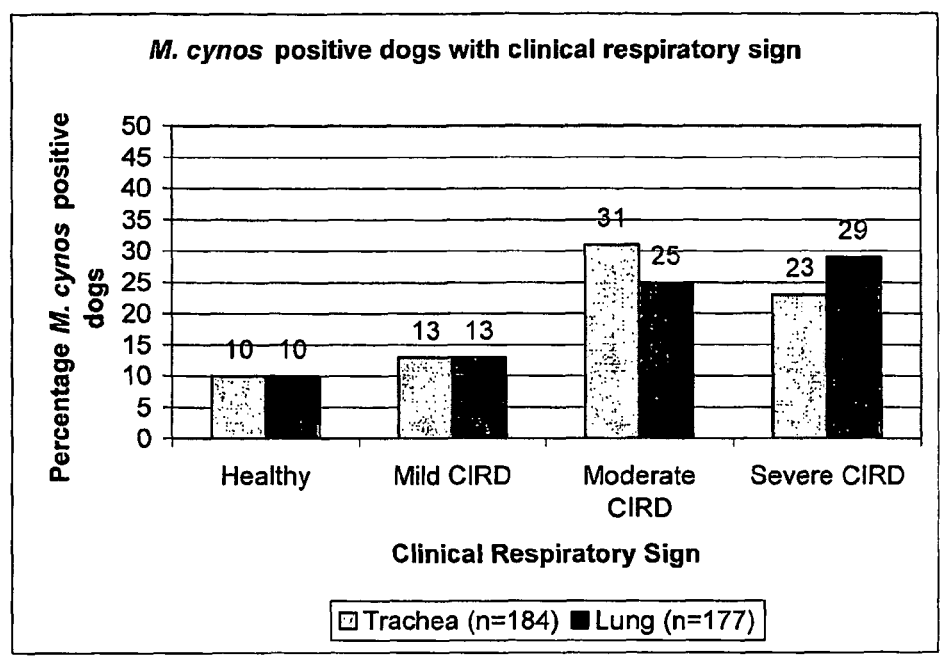
FIG. 3: Percentage of dogs with tracheal and lung *M. cynos* infection at increasing levels of severity of CIRD.

The Association of *Mycoplasma cynos* with Canine Infectious Respiratory Disease The presence of *M. cynos* was investigated by culture of the organism and identification by PCR analysis. In a survey of 184 kennelled dogs we have found that the percentage of dogs with *M. cynos* in the trachea or lung increases with signs of respiratory disease from 10% in healthy dogs to 31% in diseased dogs (FIG. 3).

Figure 4:
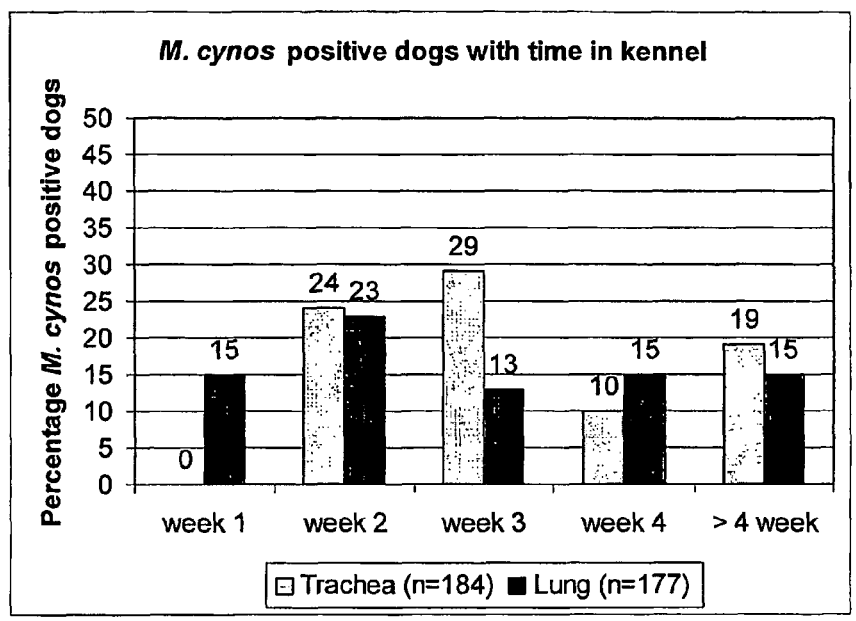
FIG. 4: Percentage of dogs with tracheal and lung *M. cynos* infection after increasing lengths of time in kennels.

We have also noted that respiratory disease increases with time in the kennel and during the first week in the kennel dogs have no detectable *M. cynos* in the trachea, whereas by the second week 24% of the 184 dogs were positive for *M. cynos* in the trachea—indicating 24% of the population are being infected with this bacterium. A smaller but similar increase was also seen for colonisation of the lung (from 15% to 23%) (see FIG. 4).

Example 3

The Association of *Chlamydophila* with Canine Infectious Respiratory Disease

We surveyed 210 dogs by PCR analysis for the presence of *Chlamydophila*.

A 218 bp fragment of the 23S rRNA gene was amplified from the *Chlamydophila* by the following PCR. Reaction conditions, 95° C. 5 min (×1 cycle), 95° C. 30 seconds, 50° C. 30 seconds, 72° C. 1 minute (×40 cycles) and 72° C. 5 mins. The PCR reaction mix of 50 µl total, included 5.0 µl 10× magnesium free buffer (Promega), 1.5 mM MgCl$_2$ (Promega), 0.5 µl (0.5 Units) Taq DNA polymerase (Promega), 0.2 mM PCR nucleotide mix (Promega), 0.025 µg forward primer C1 (5'-GATGCCTTGGCATTGATAGGC-GATGAAG GA-3', SEQ ID NO: 9) and reverse primer C2 (5'-TGGCTCATCATGCAAAAGGCA-3', SEQ ID NO: 10), 40 µl water and 2 µl sample tissue DNA.

Figure 7:
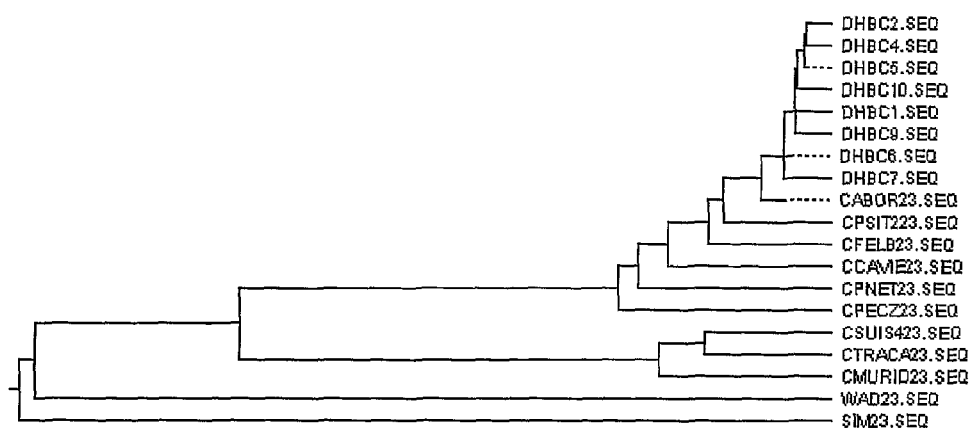
FIG. 7: Partial 23S rRNA canine sequences (DHB) aligned with the 23S rRNA of all known species of *Chlamydia* and *Chlamydophila* (Cabor—*C. abortus*, Cpsit—*C. psittaci*, Cfel—*C. felis*, Ccavi—*C. caviae*, Cpne—*C. pneumoniae*, Cpec—*C. pecorum*, Csuis—*C. suis*, Ctrac—*C. trachomatis*, Wad—*Waddlia*, Sim—*Simkania*).

A PCR product obtained from 8 dogs was confirmed as a *Chlamydophila* by sequence analysis and comparison of the PCR product to all available sequences in GenBank by Fasta analysis. The partial sequence of the 23S rRNA gene of one such sequence (DHBC10) is shown in FIG. 5 (SEQ ID NO: 1). This 218 bp sequence is 99.08% identical to the same region in *Chlamydophila abortus* and 98.6% identical to *Chlamydophila psittaci* and 96.3% identical to *Chlamydophila felis* and on preliminary phylogenetic analysis (clustal method with Megalign) most sequences cluster in a distinct clade (FIG. 7). The 23S rRNA partial sequences of seven other *Chlamydophila* isolates are shown in FIG. 8 (SEQ ID NOs: 2-8).

Figure 6:
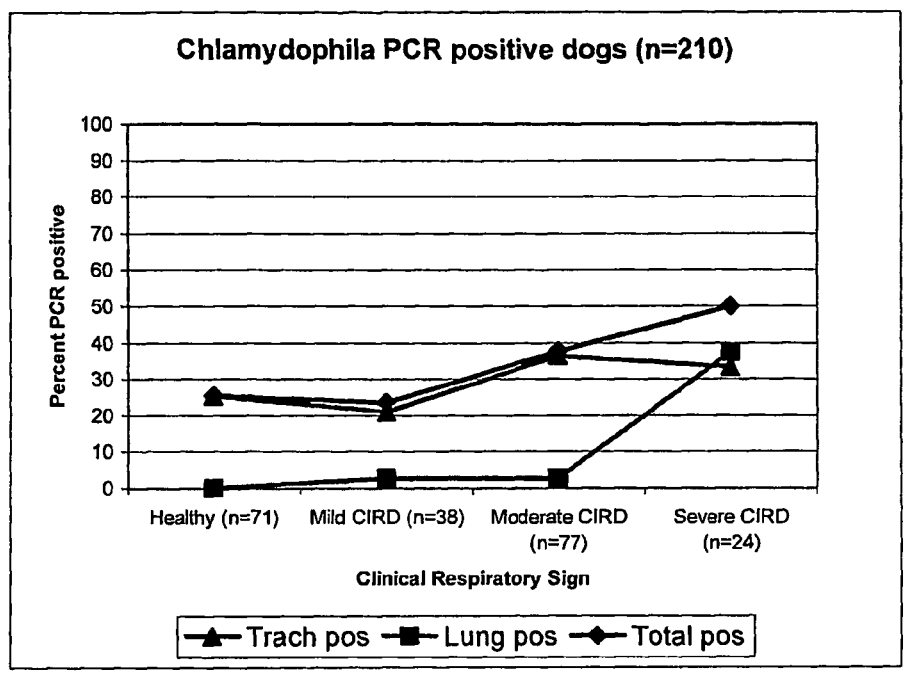
FIG. 6: Percentage of dogs with tracheal and lung *Chlamydophila* infection at increasing levels of severity of CIRD.

In this survey we found an increase in the detection of *Chlamydophila* with increasing respiratory disease severity in both the trachea and lung. A slight increase of detection of 10% was found in tracheal samples (from 25% to 34%). A more dramatic difference was found in detection of *Chlamydophila* in the lung, with an increase from 0% healthy dogs to 37.5% in dogs with CIRD (FIG. 6). Furthermore, an increase in the total number of dogs that tested positive by PCR for *Chlamydophila* from 25% in healthy dogs to 50% in dogs with severe disease was noted (FIG. 6).

Example 4

Figure 9:
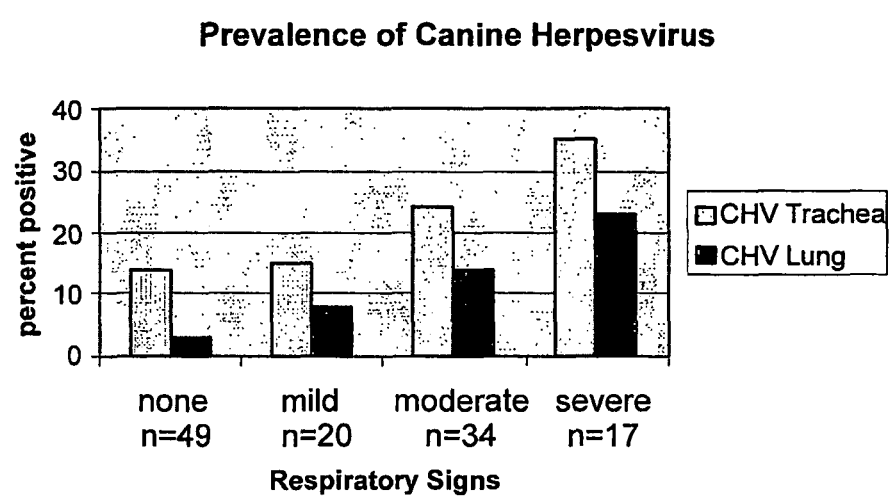
FIG. 9: Percentage of dogs with tracheal and lung canine herpesvirus infection at increasing levels of severity of CIRD.

The Association of Canine Herpesvirus with Canine Infectious Respiratory Disease We found an increased prevalence of canine herpesvirus in dogs with more severe respiratory symptoms (FIG. 9). When monitoring antibody responses to CHV over a yearlong period, dogs in a kennel with frequent outbreaks of respiratory disease showed seroconversions to CHV more frequently (58.3%) than dogs from a comparable kennel with no outbreaks (8.3%).

REFERENCES

Angus, J. C., Jang, S. S., Hirsh. D. C., (1997). Microbiological study of transtracheal aspirates from dogs with suspected lower respiratory tract disease: 264 cases (1989-1995). *J. Am. Vet. Med. Assoc.* 210, 55-58.

Anzai, T., Walker, J. A., Blair, M. B., Chambers, T. M., Timoney, J. F., (2000). Comparison of the phenotypes of *Streptococcus zooepidemicus* isolated from tonsils of healthy horses and specimens obtained from foals and donkeys with pneumonia. *Am. J. Vet. Res.* 61, 162-166.

Appel M J, Percy D H. SV-5-like parainfluenza virus in dogs. (1970) *J Am Vet Med Assoc.* 1970 Jun. 15; 156(12):1778-81

Appel, M., Binn, L. N., 1987. Canine Infectious Tracheobronchitis Short review: Kennel Cough. In: Appel M. (Ed.), Virus Infections of Carnivores. Elsevier. Oxford. pp. 201-211.

Arizmendi F, Grimes J E, Relford R L. (1992). Isolation of *Chlamydia psittaci* from pleural effusion in a dog. *J. Vet Diagn Invest.* 4(4): 460-3.

Azetaka, M., Konishi, S., (1988). Kennel cough complex: confirmation and analysis of the outbreak in Japan. *Jap. J. Vet. Sci.* 50, 851-858.

Balter, S., Benin, A., Pinto, S. W. L., Teixeira, L. M., Alvim, G. G., Luna, E., Jackson, D., LaClaire, L., Elliot, J., Facklam, R., Schuchat, A., (2000). Epidemic nephritis in Nova Serrana, Brazil. *Lancet.* 355, 1776-1780.

Barile, M. F. (1985) Immunization against mycoplasma infections p 451-492. In S. Razin and M. F. Barile (Ed.) The Mycoplasamas, vol 4. Mycoplasma pathogenicity. Academic Press, Inc, Orlando, Fla.

Barile M. F. et al., (1985). Current status on the controls of mycoplasma diseases of man, animals, plants and insects. *Bull. Inst. Pasteur.* 83: 339-373.

Bemis, D. A., Carmichael, L. E., and Appel, M. J. (1977a). Naturally occurring respiratory disease in a kennel caused by *Bordetella bronchiseptica*. *Cornell Vet.* 67, 282-93.

Bemis D A, Greisen H A, and Appel M J. (1977b). Pathogenesis of canine bordetellosis. *J. Infect Dis* 135:753-762.

Biberstein, E. L., Brown, C., Smith, T., (1980). Serogroups and Biostypes among beta-hemolytic streptococci of canine origin. *J. Clin. Microbiol.* 11, 558-561.

Biberstein, E. L., Hirsh, D. C., (1999). Streptococci. In: Hirsh, D. C., Zee, Y. C., (Eds.) Veterinary Microbiology. Blackwell Science. Oxford. pp 120-126.

Binn, L. N., Eddy, G. A., Lazar, E. C., Helms, J., and Murnane, T. (1967). Viruses recovered from laboratory dogs with respiratory disease. *Proc Soc Exp Biol Med* 126, 140-5

Chalker V J, Toomey C, Opperman S, Brooks H W, Ibuoye M A, Brownlie J, Rycroft A N. Respiratory Disease in Kennelled Dogs: Serological Responses to *Bordetella bronchiseptica* Lipopolysaccharide Do Not Correlate with Bacterial Isolation or Clinical Respiratory Symptoms. *Clin Diagn Lab Immunol.* 10(3):352-6. 2003

Chanter, N., (1997) Streptococci and enterococci as animal pathogens. *J. Appl. Microbiol. Symp. Suppl.* 83, 100S-109S.

Cocoran, B. (1998). Cytological collection techniques. In: Luis Fuentes, V. Swift, S., (Eds.), Manual of small animal cardiorespiratory medicine and surgery. *British Small Anim. Vet. Assoc.* Cheltenham. pp. 75-79.

Ditchfield, J., Macpherson, L. W., and Zbitnew, A. (1962). Association of a canine adenovirus (Toronto A 26/61) with an outbreak of laryngotracheitis ("kennel cough"). *Can. Vet. Jour.* 3, 238-247

Ellis J A, Haines D M, West K H, Burr J H, Dayton A, Townsend H G, Kanara E W, Konoby C, Crichlow A, Martin K, Headrick G. (2001) Effect of vaccination on experimental infection with *Bordetella bronchiseptica* in dogs. *J Am Vet Med Assoc.* 218(3):367-75.2001

Erles, K., Toomey, C., Brooks, H. W., Brownlie, J. (2003). Detection of a group 2 coronavirus in dogs with canine infectious respiratory disease. *Virology.* In press.

Farrow J A, et al. (1984). "Taxonomic studies on Streptococci of serological groups C, G and L and possibly related taxa". *Syst. Appl. Microbiol.* 5: 483-493.

Fraser G, Norval J, Withers A R, Gregor W W. (1985) A case history of psittacosis in the dog. *Vet Rec.* 1969 85(3): 54-8.

Fukushi H, Ogawa H, Minamoto N, Hashimoto A, Yagami K, Tamura H, Shimakura S, Hirai K. (1985) Seroepidemiological surveillance of *Chlamydia psittaci* in cats and dogs in Japan. Vet Rec. 117(19): 503-4.

Garnett, N. L., Eydelloth, R. S., Swindle, M. M., Vonderfecht, S. L., Strandberg, J. D., Luzarraga, M. B., (1982). Hemorrhagic streptococcal pneumonia in newly procured research dogs. *J. Am. Vet. Med. Assoc.* 181, 1371-1374.

Gresham A C, Dixon C E, Bevan B J. (1996) Domiciliary outbreak of psittacosis in dogs: potential for zoonotic infection. *Vet Rec.* 138(25):622-3.

Jang S S, Ling G V, Yamamoto R, Wolf A M. (1984) Mycoplasma as a cause of canine urinary tract infection. *J Am Vet Med Assoc* 185(1):45-7

Karpas, A., King, N. W., Garcia, F. G., Calvo, F., and Cross, R. E. (1968a). Canine tracheobronchitis: Isolation and characterization of the agent with experimental reproduction of the disease. *Proc Soc Exp Biol Med.* 127, 45-52.

Karpas A, Garcia F G, Calvo F, Cross R E. (1968b) Experimental production of canine tracheobronchitis (kennel cough) with canine herpesvirus isolated from naturally infected dogs. *Am J Vet Res.*29(6):1251-7.

Keil, D. J., and Fenwick, B. (1998). Role of *Bordetella bronchiseptica* in infectious tracheobronchitis in dogs. *J Am Vet Med Assoc.* 15, 200-7.

Lambrechts N, Picard J, Tustin R C. (1999) *Chlamydia*-induced septic polyarthritis in a dog. *J. S Afr Vet Assoc.* 70(1):40-2).

Lou, T. Y., and Wenner, H. A. (1963). Natural and experimental infection of dogs with reovirus, type1: pathogenicity of the strain for other animals. *Am. J. Hyg.* 77, 293-304.

McCandlish, I. A. P., Thompson, H., Cornwell, H. J. C., Wright, N. G., 1978. A study of dogs with kennel cough. *Vet. Rec.* 102, 298-301.

McKiernan, B. C., Smith, A. R., Kissil, M., 1982. Bacterial Isolates from the lower trachea of clinically healthy dogs. *J. Am. Anim. Hospl. Assoc.* 20, 139-142.

Quinn, P. J., Carter, M. E., Markey, B. K., Carter, G. R., (Eds.), 1999. Clinical Veterinary Microbiology. Mosby. pp. 129-130.

Randolph J F, Moise N S, Scarlett J M, Shin S J, Blue J T, Bookbinder P R. (1993). Prevalence of mycoplasmal and ureaplasmal recovery from tracheobronchial lavages and prevalence of mycoplasmal recovery from pharyngeal swab specimens in dogs with or without pulmonary disease. *Am J Vet Res. March;* 54(3):387-91.

Rosendal, S. (1972). *Acta Vet. Scand.* 13: 137.

Rosendal & Vinther (1977). Experimental mycoplasmal pneumonia in dogs: electron microscopy of infected tissue. *Acta Pathol Microbiol Scand [B]* 85B(6):462-5.

Rosendal, S. (1978). Canine Mycoplasmas: Pathogenicity of Mycoplasmas associated with distemper pneumonia. *J. Infect. Dis.* 138(2), 203-210.

Sadatsune, T., Moreno, G., 1975. Contribution to the study of b-haemolytic streptococci isolated from dogs. *Arq. Inst. Biol. Sao. Paulo.* 42, 257-264.

Sako T, Takahashi T, Takehana K, Uchida E, Nakade T, Umemura T, Taniyama H. (2002) Chlamydial infection in canine atherosclerotic lesions. *Atherosclerosis.* 162(2): 253-9.

Smith J. E., 1967. The aerobic bacteria of the nose and tonsils of healthy dogs. *J. Comp. Path.* 71, 428-433.

Storz, J. (1988) Microbiology of *Chlamydia*. p. 168 Ed A. L. Barron, Boca Raton, CRC Press.

Swango L J, Wooding W L Jr, Binn L N. 1970. A comparison of the pathogenesis and antigenicity of infectious canine hepatitis virus and the A26-61 virus strain (Toronto). *J Am Vet Med Assoc.* 1970 Jun. 15; 156(12):1687-96.

Thompson H, McCandlish I A P, Wright N G: (1976) Experimental respiratory disease in dogs due to *Bordetella bronchiseptica*. *Res Vet Sci* 20:16-23.

Thrusfield, M. V., Aitken, C. G. G., Murihead, R. H., (1991). A field investigation of kennel cough: incubation period and clinical signs. *J. Small Anim. Pract.* 32, 215-220.

Timoney, J. F. (1987). The Streptococci. In: Gyles, C. L., Thoen C. O., (Eds.) Pathogenesis of bacterial infections in animals. Iowa State University Press. pp. 12-13.

Timoney, J. F., Gillespie, J. H., Scott, F. W., Barlough, J. E., (Eds), 1988. The Genus *Streptococcus*. In: Hagan and Bruner's Microbiology and Infectious Diseases of Domestic Animals. Comstock Publishing Associates, London. pp. 181-187.

Ural O, Tuncer I, Dikici N, & Aridogan B. (2003). *Streptococcus zooepidemicus* meningitis and bacteraemia. *Scand J Infect Dis.* 35(3): 206-207.

Walker, J. A., Timoney, J. F., (1998). Molecular basis of variation in protective SzP proteins of *Streptococcus zooepidemicus*. *Am. J. Vet. Res.* 59, 1129-1133.

Walker R L & Runyan C A (2003). Identification of variations in SzP proteins of *Streptococcus equi* subspecies *zooepidemicus* and the relationship between protein variants and clinical signs of infection in horses. *Am J Vet Res.* 64(8): 976-81.

Werth D, Schmeer N, Muller H P, Karo M, Krauss H. (1987). Demonstration of antibodies against *Chlamydia psittaci* and *Coxiella burnetii* in dogs and cats: comparison of the enzyme immunoassay, immunoperoxidase technic, complement fixation test and agar gel precipitation test *Zentralbl Veterinarmed B.* 34(3): 165-76.

Wood, J. L. N., Burrell, M. H., Roberts, C. A., Chanter, N., Shaw, Y., (1993). Streptococci and *Pasteurella* spp. associated with disease of the equine lower respiratory tract. *Equine Vet. J.* 25, 314-318.

Young S, Storz J, Maierhofer C A. (1972) Pathologic features of experimentally induced chlamydial infection in dogs. *Am J Vet Res.* 33(2): 377-83.

What is claimed is:

1. An immunogenic composition comprising:
   (a) a first agent capable of raising an immune response against *Mycoplasma cynos* (*M. cynos*) in a dog, and
   (b) a second agent comprising one or more agents selected from the group consisting of:
      (i) an agent capable of raising an immune response against *Streptococcus equi* sub species *zooepidemicus* (*S. zooepidemicus*) in a dog, and
      (ii) an agent capable of raising an immune response against a *Chlamydophila* in a dog;
   wherein said first agent comprises inactivated or attenuated *M. cynos* and said second agent comprises: (i) inactivated or attenuated *S. zooepidemicus*, or (ii) inactivated or attenuated *Chlamydophila abortus, Chlamydophila felis, Chlamydia muridarum, Chlamydia pecorum, Chlamydia pneumoniae, Chlamydia suis* or *Chlamydia trachomatis*.

2. A pharmaceutical composition comprising an immunogenic composition according to claim 1 and a pharmaceutically acceptable carrier, diluent or adjuvant.

3. The immunogenic composition according to claim 1 further comprising any one or more of:
   an agent capable of raising an immune response in a dog against canine respiratory coronavirus (CRCV), wherein said CRVC is a Group II coronavirus;
   an agent capable of raising an immune response in a dog against canine parainfluenzavirus (CPIV);
   an agent capable of raising an immune response in a dog against canine adenovirus type 2 (CAV-2);
   an agent capable of raising an immune response in a dog against canine herpesvirus (CHV); and
   an agent capable of raising an immune response in a dog against *Bordetella bronchiseptica* (*B. bronchiseptica*).

4. An immunogenic composition according to claim 3 wherein the agent capable of raising an immune response in a dog against CRCV comprises inactivated or attenuated CRCV.

5. An immunogenic composition according to claim 3 wherein the agent capable of raising an immune response in a dog against CRCV comprises a Spike protein or a hemagglutinin-esterase (HE) protein of CRCV, or an immunogenic portion of the Spike or HE protein.

6. An immunogenic composition according to claim 3 wherein the agent capable of raising an immune response in a dog against CPIV comprises inactivated or attenuated CPIV.

7. An immunogenic composition according to claim 3 wherein the agent capable of raising an immune response in a dog against CAV-2 comprises inactivated or attenuated CAV-2.

8. An immunogenic composition according to claim 3 wherein the agent capable of raising an immune response in a dog against CHV comprises inactivated or attenuated CHV.

9. An immunogenic composition according to claim 3 wherein the agent capable of raising an immune response in a dog against *B. bronchiseptica* comprises inactivated or attenuated *B. bronchiseptica*.

10. A method of eliciting an immune response in a dog comprising administering to the dog an immunogenic composition according to claim 1.

11. A method of stimulating an immune response against *M. cynos* and an organism selected from *S. zooepidemicus* and a *Chlamydophila*, the method comprising administering to a dog an immunogenic composition according to claim 1, wherein said immunogenic composition stimulates an immune response against *M. cynos* and an organism selected from *S. zooepidemicus* and a *Clamydophila* in the dog.

12. The method according to claim 11 further comprising administering to the dog any one or more of:
   an agent capable of raising an immune response in a dog against CRCV, wherein said CRVC is a Group II coronavirus;
   an agent capable of raising an immune response in a dog against CPIV;
   an agent capable of raising an immune response in a dog against CAV-2;
   an agent capable of raising an immune response in a dog against CHV; and
   an agent capable of raising an immune response in a dog against *B. bronchiseptica*.

13. An immunogenic composition comprising:
   (a) a first agent capable of raising an immune response against *Mycoplasma cynos* (*M. cynos*) in a dog, wherein said first agent comprises inactivated or attenuated *M. cynos*;
   (b) a second agent capable of raising an immune response against *Streptococcus equi* sub species *zooepidemicus* (*S. zooepidemicus*) in a dog, wherein said first agent comprises inactivated or attenuated *S. zooepidemicus*; and
   (c) a third agent capable of raising an immune response against a *Chlamydophila* in a dog, wherein said first agent comprises inactivated or attenuated *Chlamydophila abortus, Chlamydophila felis, Chlamydia muridarum, Chlamydia pecorum, Chlamydia pneumoniae, Chlamydia suis* or *Chlamydia trachomatis*.

* * * * *

UNITED STATES PATENT AND TRADEMARK OFFICE
CERTIFICATE OF CORRECTION

| | | |
|---|---|---|
| PATENT NO. | : 8,329,194 B2 | Page 1 of 2 |
| APPLICATION NO. | : 10/563199 | |
| DATED | : December 11, 2012 | |
| INVENTOR(S) | : Brownlie et al. | |

It is certified that error appears in the above-identified patent and that said Letters Patent is hereby corrected as shown below:

On the Title Page
    Page 1, Item [56], column 2, line 17, under Other Publications, please change "1994." to --1994).--.
    Page 2, Item [56], column 1, line 9, under Other Publications, please change "chracterization" to --characterization--.
    Page 2, Item [56], column 1, line 27, under Other Publications, please change ""Coronviridae"" to --"Coronaviridae"--.
    Page 2, Item [56], column 1, line 29, under Other Publications, please change "Wein," to --Wien,--.
    Page 2, Item [56], column 2, line 7, under Other Publications, please change "Parachlamydiacease" to --Parachlamydiaceae--.
    Page 2, Item [56], column 2, line 57, under Other Publications, please change ""Huuman" to --"Human--.
    Page 2, Item [56], column 2, line 70, under Other Publications, please change "coronoviruses" to --coronaviruses--.
    Page 3, Item [56], column 1, line 12, under Other Publications, please change "oligonucletode" to --oligonucleotide--.
    Page 3, Item [56], column 1, line 17, under Other Publications, please change "epitherlial" to --epithelial--.
    Page 3, Item [56], column 2, line 24, under Other Publications, please change "Chlamydiacae"" to --Chlamydiaceae"--.
    Page 4, Item [56], column 1, line 40, under Other Publications, please change "antiysozyme" to --antilysozyme--.
    Page 4, Item [56], column 2, line 3, under Other Publications, please change "Streptococacaceae" to --Streptococcaceae--.
    Page 4, Item [56], column 2, line 41, under Other Publications, please change "Veternary" to --Veterinary--.
    Page 4, Item [56], column 2, line 52, under Other Publications, please change "Traceobronchitis"" to --Tracheobronchitis"--.

Signed and Sealed this
Seventh Day of January, 2014

Margaret A. Focarino
*Commissioner for Patents of the United States Patent and Trademark Office*

CERTIFICATE OF CORRECTION (continued)
U.S. Pat. No. 8,329,194 B2

In the Specifications

Column 2, line 56, please change "of of" to --of--.
    Column 3, line 33, please change "athrosclerosis" to --atherosclerosis--.
    Column 3, line 45, please change "athrosclerosis," to --atherosclerosis,--.
    Column 6, line 40, please change "antigenicity" to --antigenicity--.
    Column 8, line 42, please change "kDA" to --kDa--.
    Column 8, line 57, please change "B-577" to --B-577.--.
    Column 9, line 32, please change "kD" to --kDa--.
    Column 15, line 46, please change "comprises" to --comprises:--.
    Column 18, line 33 (approx.), please change "comprises" to --comprises:--.
    Column 20, line 53, please change "F(ab'$_2$," to --F(ab')$_2$,--.
    Column 21, line 54, please change "Chimaeric" to --Chimeric--.
    Column 23, line 38, please change "amplication," to --amplification,--.
    Column 24, line 9, please change "(TMACI)" to --(TMACl)--.
    Column 24, line 14, please change "milk" to --milk.--.
    Column 25, line 29-30, please change "antibody antibody." to --antibody.--.
    Column 28, line 22, please change "haemtoxylin" to --haematoxylin--.
    Column 29, line 3, please change "GrapbPad" to --GraphPad--.
    Column 32, line 66, please change "Mycoplasamas," to --Mycoplasmas,--.
    Column 35, line 16 (approx.), please change "Chlamidophila" to --Chlamydophila--.

In the Claims

Column 39, line 39, in Claim 3, please change "CRVC" to --CRCV--.
    Column 40, line 32, in Claim 11, please change "Clamydophila" to --Chlamydophila--.
    Column 40, line 36, in Claim 12, please change "CRVC" to --CRCV--.

SEQUENCE LISTING

```
<160> NUMBER OF SEQ ID NOS: 10

<210> SEQ ID NO 1
<211> LENGTH: 218
<212> TYPE: DNA
<213> ORGANISM: Chlamidophila

<400> SEQUENCE: 1
agtggtctcc ccagattcag actaggtttc acgtgcctag ccctactcag gtatcgaata      60
gagtctcttg ttttttcgtc tacgggacta tcaccctgta tcgttctact ttccagaagt    120
attcgactaa aacttaagat cccatgttat cgaccctaca accccacatt aaaaatgtgg    180
tttggtcttc tccccttcg ctcgccgcta cacaggga                              218

<210> SEQ ID NO 2
<211> LENGTH: 221
<212> TYPE: DNA
<213> ORGANISM: Chlamydophila

<400> SEQUENCE: 2
gacagtggtc tccccagatt cavactaggt ttcacgtgtc tagccctact caggtatcga     60
atagagtctc ttgttttttwc gtctacggga ctatcaccct gtatcgttct actttccaga   120
agtattcgac taaaacttaa gatcccatgt tatcgaccct acaaccccac attaaaaatg    180
tggtttggtc ttctcccctt cgctcgccg ctacacaggg a                         221

<210> SEQ ID NO 3
<211> LENGTH: 224
<212> TYPE: DNA
<213> ORGANISM: Chlamydophila

<400> SEQUENCE: 3
tgagagtggt ctcccagat tcagactagg tttcacgtgt ctagccctac tcaggtatcg      60
aatagagtct cttgttttt cgtctacggg actaacaccc tgtatcgttc tactttccag    120
aagtattcga ctaaaactta agatcccatg ttatcgaccc tacaacccca cattaaaaat    180
gtggtttggt cttctcccct tttcgctcgk ccgytatcac aggg                     224

<210> SEQ ID NO 4
<211> LENGTH: 221
<212> TYPE: DNA
<213> ORGANISM: Chlamydophila

<400> SEQUENCE: 4
gadagtggtc tccccagatt cadactaggt ttcacgtgtc tagccctact caggtatcga     60
atagagtctc ttgttttttc gtctacggga ctatcaccct gtatcgttct actttycaga   120
agtattcgac taawwcttaa gatcccatgt tatcgaccct acaaccccac attwwwwatg    180

```
tggtttggtc ttctccccttt tygctcgccg ctacacaggg a                          221
```

```
<210> SEQ ID NO 5
<211> LENGTH: 217
<212> TYPE: DNA
<213> ORGANISM: Chlamydophila

<400> SEQUENCE: 5
tgagagtggt ctccccagat tcagactagg tktcacgtgt ctagccctac tcaggtatcg      60
aatagagtct cttgttttkt cgtctacggg actatcaccc tgtatcgttc tactttccca    120
gaagtattcg actaaaahct taagatcccc atgttatcga ccctacaacc cccacataaa    180
aaatgtggtt tggtcttctc ccctttcgct cgccgct                              217
```

```
<210> SEQ ID NO 6
<211> LENGTH: 221
<212> TYPE: DNA
<213> ORGANISM: Chlamydophila

<400> SEQUENCE: 6
gabagtggtc tccccagatt cagactaggt ttcacgtgtc tagccctact caggtatcga     60
atagagtctc ttgttttttc gtctacggga ctatcaccct gtatcgttct actttccaga    120
agtattcgac taaaacttaa gatcccatgt tatcgaccct acaaccccac attaaaaatg    180
tggtttggtc ttctcccctt tcgctcgccg ctactcaggg a                         221
```

```
<210> SEQ ID NO 7
<211> LENGTH: 220
<212> TYPE: DNA
<213> ORGANISM: Chlamydophila

<400> SEQUENCE: 7
tgagagtggt ctccccagat tcagtcaaaa tatcacgtgt tccgacctac tcaggatact     60
attagtatta ttgagaatbt taattacagg agtatcacct tctatgctct agtttccaac    120
taattcatct attctcttta attacacatt atagtcctac aaccccmaa tgcaagcatt     180 gggtttgtcc taatcccagt tcgctcgccg ctacacaggg                           220
```

```
<210> SEQ ID NO 8
<211> LENGTH: 220
<212> TYPE: DNA
<213> ORGANISM: Chlamydophila
<220> FEATURE:
<221> NAME/KEY: misc_feature
<222> LOCATION: 174
<223> OTHER INFORMATION: n = A,T,C or G

<400> SEQUENCE: 8
tgagagtggt ctccccagat tcagactagg tttcacgtgt ctagccctac tcaggtatcg     60
aatagagtct cttgtttttt tgtctacggg actatcaccc tgtatcgttc tactttccag    120
aagtattcga ctaaaactta agatcccatg ttatcgaccc tacaacccca catnaaaaat    180
gtggtttggt cttctcccct ttcgctcgcc gctacacagg                           220
```

```
<210> SEQ ID NO 9
<211> LENGTH: 28
<212> TYPE: DNA
<213> ORGANISM: Artificial Sequence
<220> FEATURE:
<223> OTHER INFORMATION: PCR primer

<400> SEQUENCE: 9
```

```
gatgccttgg cattgatagg cgatgaag                                              28

<210> SEQ ID NO 10
<211> LENGTH: 21
<212> TYPE: DNA
<213> ORGANISM: Artificial Sequence
<220> FEATURE:
<223> OTHER INFORMATION: PCR primer

<400> SEQUENCE: 10
tggctcatca tgcaaaaggc a                                                     21
```